US006421650B1

(12) United States Patent
Goetz et al.

(10) Patent No.: US 6,421,650 B1
(45) Date of Patent: Jul. 16, 2002

(54) MEDICATION MONITORING SYSTEM AND APPARATUS

(75) Inventors: Gerald E. Goetz, Penn Valley, CA (US); Terry Precht; Eric Krug, both of Loveland, CO (US); Andrew Fanton, Westminster, CO (US); Joe Keating, Lafayette, CO (US); Brian Coppom, Boulder, CO (US); Bradley Thompson, Denver, CO (US); Brian Hepp, Berthoud, CO (US)

(73) Assignee: Goetech LLC, Denver, CO (US)

( * ) Notice: Subject to any disclaimer, the term of this patent is extended or adjusted under 35 U.S.C. 154(b) by 0 days.

(21) Appl. No.: 09/260,936

(22) Filed: Mar. 2, 1999

Related U.S. Application Data

(63) Continuation-in-part of application No. 09/261,044, filed on Mar. 2, 1999.
(60) Provisional application No. 60/076,943, filed on Mar. 4, 1998, and provisional application No. 60/093,753, filed on Jul. 22, 1998.

(51) Int. Cl.[7] ............................................. G06F 17/60

(52) U.S. Cl. ............................... 705/3; 705/2; 702/177; 368/10; 235/375; 128/205.23; 604/20; 604/131

(58) Field of Search ........................ 705/3, 2; 702/177; 368/10; 235/375; 128/205.23; 604/20, 131

(56) References Cited

U.S. PATENT DOCUMENTS

| 4,588,303 A | | 5/1986 | Wirtschafter et al. ......... 368/10 |
| 4,695,954 A | * | 9/1987 | Rose et al. ..................... 221/15 |

(List continued on next page.)

FOREIGN PATENT DOCUMENTS

| EP | 0 298627 A3 | 1/1989 | |
| JP | 408149216 A | * 7/1996 | .......... H04M/11/00 |
| JP | 409282400 A | * 10/1997 | ........... G06F/19/00 |

OTHER PUBLICATIONS

EFT/POS On Its Way to the Health Care Market, EFT Report, v 13, n8, p5, Apr. 1990.*

(List continued on next page.)

Primary Examiner—Vincent Millin
Assistant Examiner—Jagdish Patel
(74) Attorney, Agent, or Firm—John R. Wahl; Merchant & Gould P.C.

(57) ABSTRACT

A medication management system which includes three components to assist a patient control, monitor and manage administration of prescribed medications. The system comprises a patient component having a retrievable patient database of patient medical history, prior prescribed medications and current prescribed medications, and it includes a data transfer interface, e.g., a hardwired interface, such as an RS232 interface or infrared data transfer port. The system also includes a physician component having a retrievable physician's database of medication information and an input/output device enabling a prescribing physician to enter prescription information into the physician component. The physician's database is capable of receiving and storing patient data transferred from the patient component through said data transfer interface. The system finally also includes a pharmacist component resident on a pharmacist's computer. The pharmacist's computer is adapted to interface with said patient component to transfer prescription data to said pharmacist component. At least one of or each of the physician component and the pharmacist component has the capability of searching a medication database to determine potential medication interactions with currently prescribed medications and identify those to the physician or pharmacist for selective downloading to the patient component so that the patient can be alerted to the potential interactions. The patient component has a scheduler which tracks a plurality of medication dose schedules and includes alarm functions to prompt a patient to take particular medications, reschedule them, and alert the patient to potential interactions between medications and/or provide caution information to the patient for administration of the medication.

56 Claims, 23 Drawing Sheets

U.S. PATENT DOCUMENTS

| | | | | |
|---|---|---|---|---|
| 4,712,460 A | * | 12/1987 | Allen et al. | 83/208 |
| 4,860,899 A | * | 8/1989 | McKee | 206/534 |
| 4,926,572 A | | 5/1990 | Holmes | 40/448 |
| 4,970,669 A | | 11/1990 | McIntosh et al. | 364/569 |
| 5,099,424 A | * | 3/1992 | Schneiderman | 705/3 |
| 5,157,640 A | | 10/1992 | Backner | 368/10 |
| 5,200,891 A | | 4/1993 | Kehr et al. | 364/413.01 |
| 5,239,491 A | | 8/1993 | Mucciacciaro | 364/569 |
| 5,289,157 A | | 2/1994 | Rudick et al. | 340/309.15 |
| 5,301,105 A | | 4/1994 | Cummings, Jr. | |
| 5,347,453 A | | 9/1994 | Maestre | |
| 5,408,443 A | | 4/1995 | Weinberger | 368/10 |
| 5,547,878 A | * | 8/1996 | Kell | 436/111 |
| 5,602,802 A | | 2/1997 | Leigh-Spencer et al. | 368/10 |
| 5,612,869 A | | 3/1997 | Letzt et al. | |
| 5,622,429 A | | 4/1997 | Heinze | |
| 5,657,236 A | | 8/1997 | Conkright | |
| 5,691,932 A | * | 11/1997 | Reiner et al. | 368/10 |
| 5,752,235 A | | 5/1998 | Kehr et al. | |
| 5,758,095 A | | 5/1998 | Albaum et al. | |
| 5,845,264 A | | 12/1998 | Nellhaus | |
| 5,867,821 A | | 2/1999 | Ballantyne et al. | |
| 5,884,273 A | | 3/1999 | Sattizahn et al. | |
| 5,899,998 A | | 5/1999 | McGauley | |
| 5,908,788 A | * | 6/1999 | Kell | 436/111 |
| 5,924,074 A | | 7/1999 | Evans | |
| 6,014,631 A | * | 1/2000 | Teagarden et al. | 705/3 |
| 6,055,506 A | * | 4/2000 | Frasca, Jr. | 705/3 |
| 6,073,106 A | * | 6/2000 | Rozen et al. | 705/3 |

OTHER PUBLICATIONS

Medical Malpractice Claims, Risk Management, p.67, Jun. 1994.*

Elson, Robert B., Computerized Patient Records in Primary Care Their Role in Mediating Guidline–Driven Physician Behaviour Change, Archives of Family Medicine, Aug. 1995.*

Levin, James; Computer Programs to Support Clinical Decision Making, JAMA Nov. 6, 1987.*

Gooding, C.; Technology: Healthy records/A loot at a Computer System That Helps Doctors Offer Patients a Better Service—Software at Work, *The Financial Times Page:* 14 Section: London, Nov. 1, 1994.

Watts, S.; Computers Are Good Medicine, *The Times*, Feb. 2, 1993.

Laurance, J.; Wired GPs Pave the Way to the Global clinic, *The Times*, Sep. 20, 1995.

Gonzales, A.; Rx–Process Links Docs, Pharmacists, *The Business Journal*, Mar. 15, 1996.

PR Newswire, Micro Card Technologies Inc. Unveils "Computer in a Card" That Will Reduce Credit Transaction Fraud, Aug. 27, 1984.

*About HIMSS*, 3 page printout of from http://www.himss.org, Sep. 9, 1998.

Resistant Strain: Healtheon Struggles In Efforts to Remedy Doctor's Paper Plague, *The Wall Street Journal*, Oct. 2, 1998.

*Highest Capacity Smart Cards Are Now From Cardlogix*, 2 page printout of web site, Sep. 4, 1998.

Leading Medical Information Technology into Y2K, *Military Medical Technology*, Feb. 1998.

Industry Interview—David Brooks, Group Senior Vice President, SAIC Federal Health Care Group, *Military Medical Technology*, vol. 2, Issue 4.

Is This Any Way to Run a Drugstore?, *MMT* (*Military Medical Technology*), vol. 2, Issue 4.

MediCard information from PC Pay Systems web site, Apr. 19, 1998.

Multi–Prescription Reminder, http://www.mitsi.com, Feb. 25, 1998.

Electronic Reminders, http://www.medportinc.com, Mar. 2, 1998.

What Is An e–pill Kinder Reminder?, http://www.via-mall.com, Mar. 2, 1998.

Rex PC Companion, web advertisement, Mar. 23, 1998.

Nanda Platform, web advertisement, Mar. 23, 1998.

Doctor PalmPilot web advertisement, Thomas Jefferson University web site, Mar. 9, 1998.

Pocket PDR Medical Book System, web advertisement, Mar. 23, 1998.

*Cardlogix Health Data Card Streamlines Care, Cuts Costs*, press release from http://www.cardlogix.com, Sep. 4, 1998.

*Highest Capacity Smart Cards Are Now From Cardlogix*, press release from http://www.cardlogix.com, Sep. 4, 1998.

*Health Data Card Family*, http://www.cardlogix.com, Sep. 4, 1998.

Data Packets advertisement, *Military Medical Technology*, Feb. 16, 1998.

VAQTA advertisement.

*Smart Cards*, www.cardlogix.com, Sep. 2, 1998.

New Payday for Rural Mexico: Coin Bags Are Out, Plastic Is In, The Wall Street Journal, undated.

PalmPilot/WorkPad information from http://www.timwarner.com, Mar. 9, 1998.

*Eric's PalmPilot Health Care Database*, http://www.path-com.com, Mar. 9, 1998.

Medical Communication Systems—Products, http://www.medcomsys.com, Mar. 9, 1998.

Plastic Dog Tags?, *Machine Design*, Oct. 8, 1998.

Prescription Dedication, Combining Drugs Safely Takes a Doctor–Patient Partnership, *Rocky Mountain News*, Sep. 1, 1998.

RxPhenom web advertisement, Sep. 3, 1998.

Franklin Medical Division advertisement for Nursing Organizer and Pocket PDR Medical Book System.

*Vials of the Dolls—The New Market in Adherence Devices*, http://www.thebody.com, Jan. 26, 1999.

*Drug–REAX System: Details*, http://www.micromedex.com, Jan. 28, 1998.

* cited by examiner

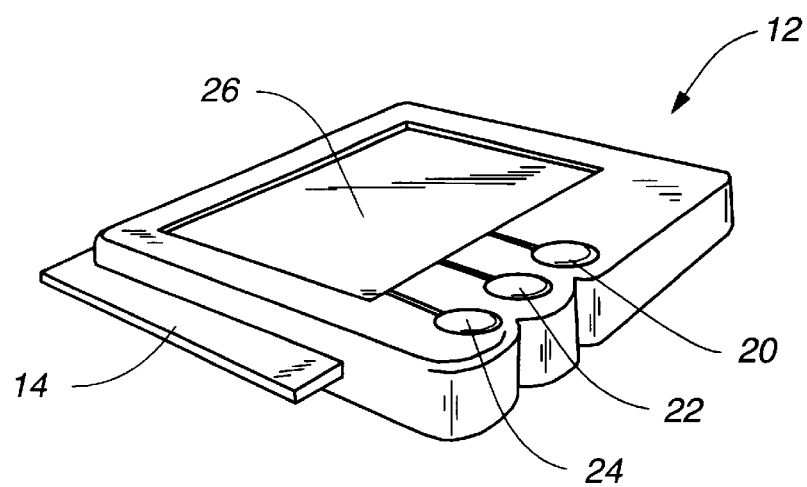
Fig. 2
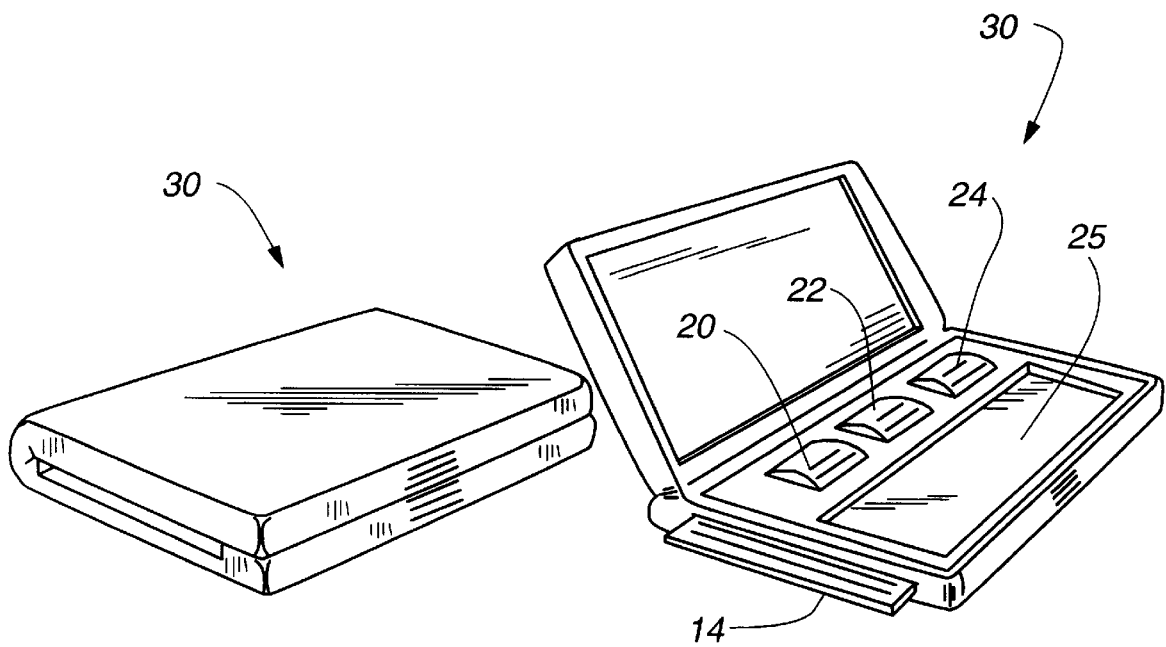
Fig. 3A  Fig. 3B

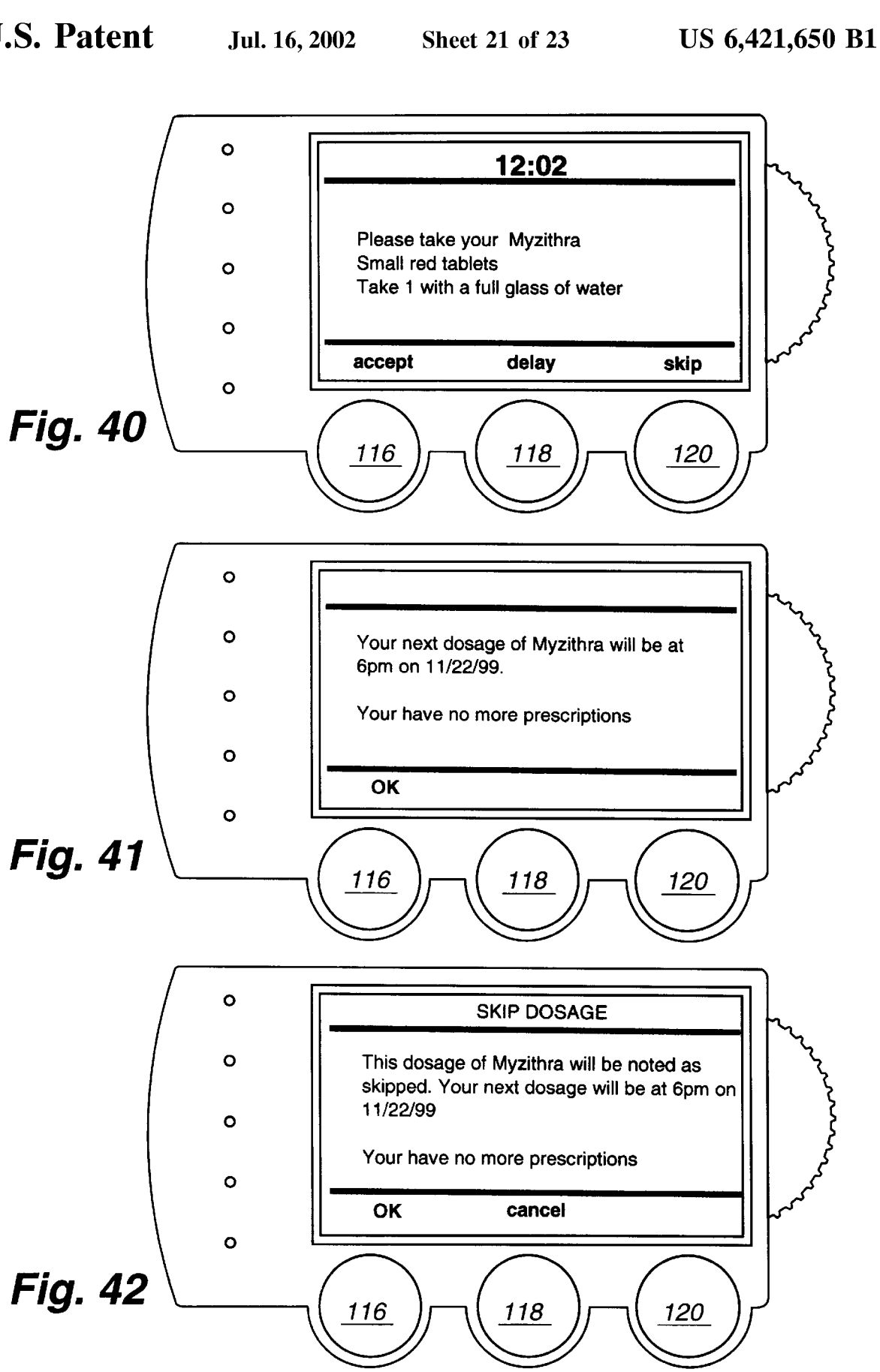

MEDICATION MONITORING SYSTEM AND APPARATUS

CROSS-REFERENCE TO RELATED APPLICATIONS

This application is a continuation-in-part of U.S. Nonprovisional Patent Application Ser. No. 09/261,044, Attorney Docket No. 41471.830001.000, entitled MEDICATION MANAGEMENT APPARATUS, filed Mar. 2, 1999 and claims the benefit of priority of the filing date of U.S. Provisional Patent Application Ser. No. 60/076,943 entitled MEDICAL MANAGEMENT APPARATUS, filed Mar. 4, 1998 and Provisional Patent Application Ser. No. 60/093, 753 entitled POCKET DOCTOR, filed Jul. 22, 1998.

BACKGROUND OF THE INVENTION

1. Field of the Invention

This invention pertains to a patient controlled personal medical information product.

2. Description of the Related Art

Medical science has created many new methods, treatments, and medications to extend and improve the lives of people. However, this has resulted in a significant increase in the medical information that a person must be aware of in order to maintain their health, and get the best benefit from these medical improvements. For example, people over the age of 55 consume a daily average of 7 different prescription medications. Each medication requires specific instructions, including warnings on correct consumption and possible side effects. Because there is such a significant increase in the amount of medical information that a person must know, such as proper use and consumption of these medications, errors can occur that adversely affect treatments and/or counteract or minimize the beneficial impact of the medications. At worst, serious injury or death has occurred due to incorrect treatments. One estimate from data shows 28% of hospitalizations are a result of "adverse drug events" and this costs the health care industry $76 billion annually (CU Doctor Sues Firm . . . Rocky Mountain News, Jun. 8, 1998).

Problems arise when either the person making the prescription, filling the prescription or consuming the prescription makes an error, or provides information that is not understood by one of the other parties in this "medical information triangle" or circle. These errors can be from transcription, misinterpretation, or insufficient information available. The most common patient originated errors are:

(a) taking incorrect doses (b) taking doses at wrong time (c) forgetting to take a dose (d) stopping medication too soon (e) taking dosage improperly, causing interactions To date, some solutions to help patients manage medications have been developed. Generally these solutions fall into two categories:

Patient Based Products

These products are reminder pill boxes and auto dispensing mechanisms. They are difficult to program, configured for a very limited number of medications, and too cumbersome to be considered a portable personal device. In particular, they did not easily link into the medical information chain and allow the physician and/or pharmacist to interact with the patient, nor did they provide complete medical information.

Medical Organization Based Products

These products are database systems run by hospitals, health maintenance organizations (HMO's) or health insurance companies. They are systems tied to these large organizations, with significant computer hardware requirements and no portability. Typically they are accessible only by physician/hospital personnel or pharmacists. In particular, the patient has no ability to control or read information at their discretion.

SUMMARY OF THE INVENTION

A system in accordance with the present invention includes a device for a patient to use to better control implementation of medication therapies. The device will, among other functions, track and display:

(a) medication name & purpose (b) dosage, frequency and duration (c) possible side effects (d) record of medications taken (e) special instructions for taking medications, such as with or without meals, fluids, avoiding sunlight, etc.

Besides information about medications, it is important for a patient to have a brief medical history that can be provided to health care providers, have a log of consumption for their medications, and maintain information about who their physicians, dentist, pharmacies, insurance providers are, and personal contact information. This data is considered critical not only during typical interaction with health care providers, but particularly in emergency medical situations. Any device that is capable of tracking the medication data a patient needs should also be capable of tracking all these other health related data.

However, it must be recognized that this medical information loop includes other personnel, as an example, physicians and pharmacists. Thus any device must be capable of allowing them to read patient data, and input information, and it must not require any significant time for them to accomplish this. In particular it must blend with day to day activities of the health care provider.

Any solution to the problem must recognize this medical information chain that primarily consists of the patient, the health care prescriber (typically the physician) and health care provider (for example, the pharmacist). The information in this chain is created on a per patient basis, making the patient the natural repositor for the information, with the prescriber (the physician) being the initiator of the information, and the provider (the pharmacist) being a source of complementary information so it is in a form useful to the patient. Thus the product must work with both medical terminology and layman's terms to promote optimum benefit of treatments and medications.

An additional requirement of any product that contains medical history information is security. Thus any product must provide maximum protection of data from access by unauthorized persons. Although many devices use PIN's to limit access and a PIN or password would be necessary for this product, the nature of the data in a device such as proposed here should also protect the data via encryption.

The present invention is a system of component devices that provides proper information to the patient to get maximum benefit from their medications, tracks medication consumption, and facilitates transfer of critical data for optimal care of the patient. It is capable of managing information, in a highly portable form for an individual patient. The system in accordance with the present invention performs and/or facilitates the following functions:

(a) Provides a record of prescription information;

(b) Maintains current and historical personal medical data;

(c) Creates and maintains a historical log of pharmaceutical agent consumption;

(d) Warns patient of side effects, interactions, and other special instructions, especially when scheduled medication times are missed or modified; and (e) Provides a vehicle for interchange data among various individuals and groups involved in patient care such as patient, physician, pharmacist, emergency medical personnel and hospital personnel.

BRIEF DESCRIPTION OF THE DRAWINGS

This invention will be more fully understood by reference to the following drawings which are for illustrative purposes only:

FIG. 2 is a perspective view of one embodiment of a patient component of the system in accordance with the invention.

FIG. 3 is a perspective view of an alternative embodiment of the patient component of the system in accordance with the invention.

FIG. 25 through 43 are a series of screens provided on the patient component as a result of the new prescription prescribed by the physician and illustrated in FIG. 22.

DETAILED DESCRIPTION OF THE INVENTION

First Embodiment

Figure 1:
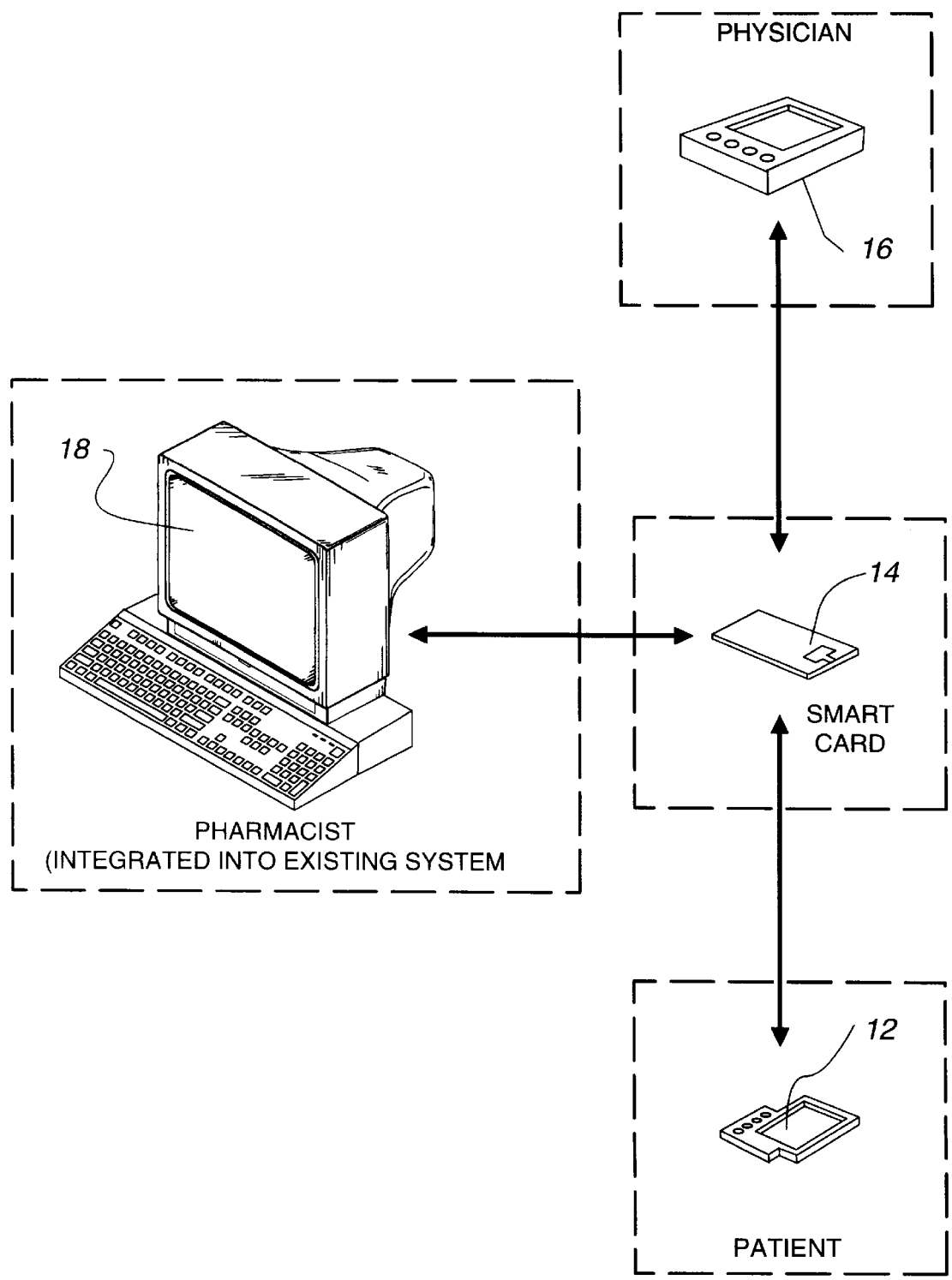
FIG. 1 is a functional system block diagram of a first embodiment of the medication management system according to the present invention.

A first embodiment of the present invention is shown functionally in FIG. 1. The system 10 comprises preferably three separate components that share a common database, where the database may be resident in the patient component 12 or contained on a memory device 14 such as a smart card. The three components of the system 10 in accordance with the present invention are a patient component 12, a physician component 16, and a pharmacist component 18.

As currently embodied, the memory device 14 is a smart card, which is an integrated circuit or chip containing a microprocessor, ROM, RAM, and EEPROM, packaged within a plastic panel much like a credit card. The memory device 14 could be manifested in a variety of other forms as well. For example, the memory device 14 may be replaced by a simple memory card which relies on the processor in one of the three components such as the patient component 12 in order to operate.

Patient Component

The patient component 12 is preferably a generally rectangular battery powered unit that has several input buttons 20, 22, and 24 along a bottom edge thereof, an LCD panel 26 visible on a front surface of the housing, and a scroll switch 28 preferably located on one edge of the housing which permits the patient/user to scroll backward and forward through the various display screens and options on the LCD as will be subsequently described. The patient component 12 basically provides the following basic functions:

1. Displays the medical data contained on the memory device or, in the smart card shown, by reading the EEPROM on the memory device 14. The display may include an ambient light sensor to adjust the contrast of the display and/or backlight of the display automatically depending on ambient light conditions.

2. Allows the patient to scroll through the data using various means to indicate, via a typical graphical user interface menu, which type of data is to be displayed.

3. Maintains date and time information.

4. Provides an alarm for when an event, such as required consumption of a medication, is to occur. The alarm can be visual, aural, or tactile.

5. Indicates dosage, frequency, special considerations in consuming the medication.

6. Provides a means to identify the type of pill to be taken such as a graphic image of the medication to be taken. (a red cylindrical pill, a blue heart shaped pill, etc.)

7. Provides information about correct consumption of the medication, including possible side effects and potential interactions with other drugs and/or consumables such as alcohol, food, milk, etc.

8. Provides a means for input by the patient via input buttons 20, 22, and 24, to indicate whether an alarmed event (e.g., time to take a medication) was accepted or delayed, and log the time, date, and action for that alarm.

9. Provides power to perform the above functions, as the smart card typically does not contain any power source of its own.

10. Is portable such that it can be carried by the patient at all times, such as in a pocket, purse, or worn with a strap on an arm, around the neck or waist. The patient component may also be provided with various attachment means, such as a magnet or hook and loop fabric to attach the unit conveniently to nearby and/or highly visible surfaces, depending on the preferences of the patient.

11. Provides security, via coding features and data encryption, to prevent unauthorized use and access to the data encoded on the smart card or within the patient component.

Two example physical configurations of the patient component are shown in FIGS. 2 and 3. The system allows a variety of devices to be used, but each one must have the capabilities to perform the prescribed unique functions. In the case of FIG. 2, the device has a slot to accept the memory device 14 or smart card, and only requires 3 buttons 20, 22, and 24 to access the data, or to prompt the patient to respond to the event alarm. The patient component 12 alarm may be audible, visual or tactile as in a vibrator device. FIG. 3 shows a device 30, much like a woman's compact, that contains a larger display area, such that an elderly patient with reduced visual acuity can still use the patient component. Each of these embodiments 12 and 30 preferably will include a button or switch control to permit the patient to scroll through display screens and an ambient light sensor coupled to the LCD to automatically adjust the contrast and back light for the display depending on ambient light conditions upon activation by the patient or the activation of an alarm event.

Physician Component

The physician component 16 is preferably a hand held personal digital assistant device such as a Palm PC or Palm Pilot type device that receives the memory device 14 and reads and writes data from and to the memory device 14. The physician component 16 is preferably programmed with at least the following basic functions:

1. Displays the medical data contained in the smart card by reading the EEPROM on the memory device 14.

2. Contains data specifically tailored for use by the physician, such as a database of diagnoses and common illnesses and correlated potential medications that may be prescribed, and a library of special instructions or treatments to be performed by the patient that the physician may prescribe.

3. Writes data to the patient's memory device 14 when it is docked in the physician component 16.

4. Optionally may include a special enclosure configuration for the use of the component 16 in areas where blood born pathogens are a concern, e.g., emergency rooms and surgical suites.

Pharmacist Component

The pharmacist component 18 is essentially a smart card reader and a software application resident on the pharmacist's personal computer which reads the physician prescription data from the memory device 14 and correctly formats the physician prescribed prescription data recorded on the memory device 14 in a form useable to the patient. This software application will reside on the same personal computer (PC) that the pharmacist currently utilizes. The time and effort for the pharmacist to provide this medication data to the patient in the patient component is designed to be very minimal, typically on the order of 15–30 seconds or less.

Nearly all pharmacists now have a personal computer in the pharmacy, with links to various health organizations, in particular organizations that provide data on both prescription and OTC medications. There is a code, known as the National Drug Code (NDC) that identifies every medication sold in the United States. In combination with this code and the access to various networked databases, the pharmacist can access and supply necessary information about the prescribed medication to the patient. Today, this data is typically printed on a sheet (typically 5.5" by 8") that contains common uses, consumption requirements, cautions and possible side effects of the particular medication. Thus the pharmacist component 18 in the system 10 of the present invention, through the pharmacist's PC, reads and write data from the pharmacist's database to the memory device 14, and will typically supply the data that is conventionally printed on the prescription information sheet to the memory device 14 in addition to medication administration instructions.

The system in accordance with the first embodiment of the invention uses smart card technology to make the link between the three easy, quick, and secure. The components may alternatively communicate via infrared serial communication links, or other communication methods such as the recently developed Personal Area Network (PAN) rather than a smart card. However, in the first preferred embodiment, a memory device 14 is utilized as the data transfer medium for illustration purposes.

Figure 4:
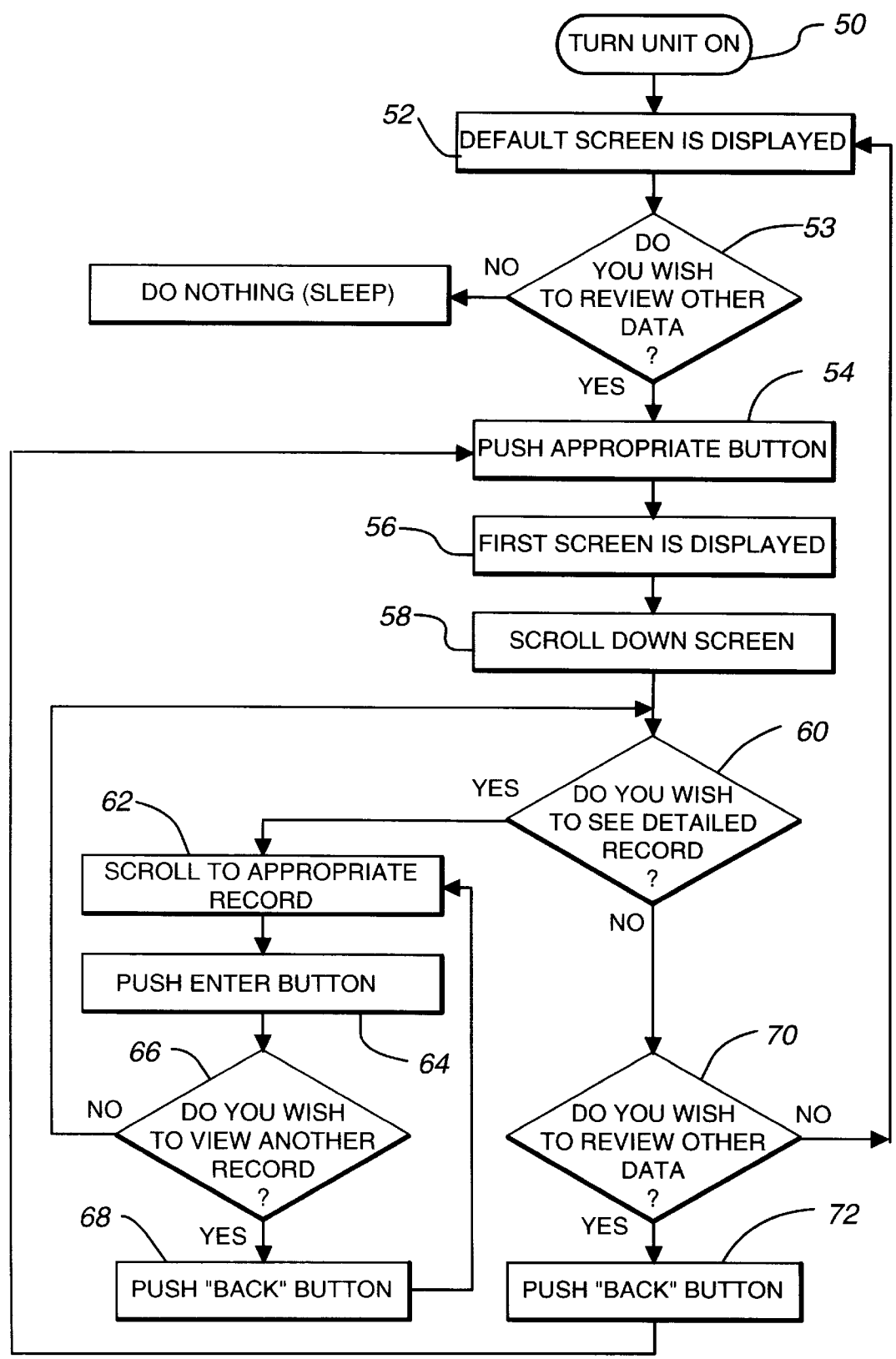
FIG. 4 is a flow diagram of the software operation of the patient components shown in FIG. 2 and FIG. 3.
Figure 5:
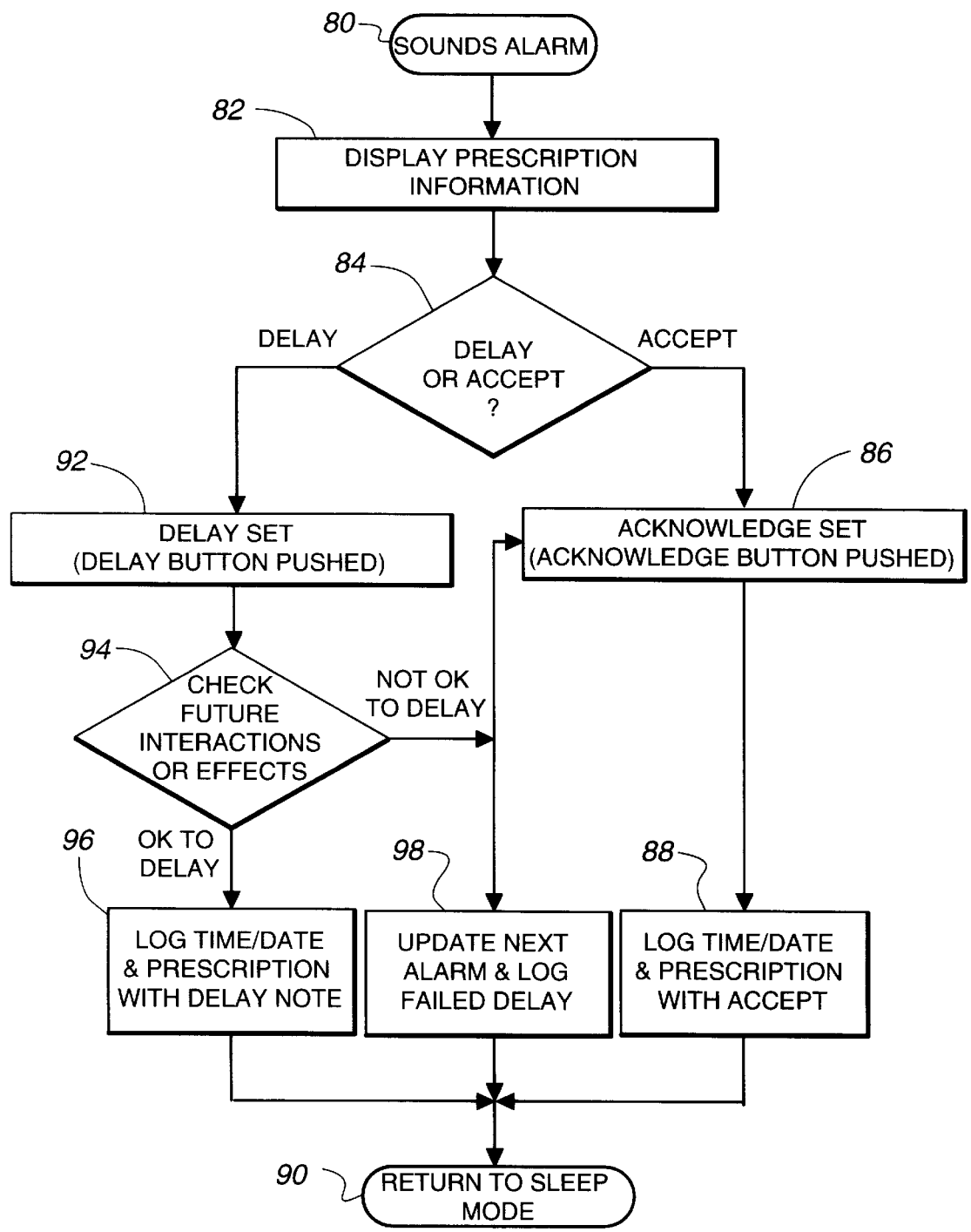
FIG. 5 is a flow chart showing a method of responding to an alarm from a patient product in accordance with the present invention.

The memory device 14 will contain at least the following data about the patient:

1. Patient Identification Information
   1.1. name, address, phones
   1.2. age, weight, height
2. Next of Kin Contact Information
   2.1. names, phones, relationships
3. Doctors
   3.1. physicians & affiliation, such as internist, dentist, optometrist
   3.2. all phone numbers and addresses
4. Insurance Information
   4.1. Company, plan identification
   4.2. contact phone
5. Patient Medication Consumption History Log
   5.1. Date & time for each medication consumed
   5.2. Date & time for a delayed medication
   5.3. Occurrence of any side effect from a medication
6. Patient Medical Conditions
   6.1. brief history
   6.2. allergies
   6.3. current conditions
   6.4. relevant family history
7. Prescription data (for every medication consumed)
   7.1. name (trade/generic) indication
   7.2. dosage, frequency, timing
   7.3. interactions
   7.4. side effects
   7.5. special instructions
   7.6. prescribing physician
   7.7. dispensing pharmacy & date filled
8. Other information
   8.1. Advertising messages for product sponsors
   8.2. Special instructions for emergency personnel
   8.3. Security access information Both of the sample patient devices shown in FIGS. 2 and 3 use the 3 button input configuration to display data and to respond to alarms. A flow diagram of the software algorithm for viewing the data on the device is shown in FIG. 4. The basic algorithm would access the data contained on the memory device 14. To respond to an alarm, a possible sequence of steps for the patient component is shown in FIG. 5.

In block 50 the patient component is turned on. Alternatively, the patient component 12 may be configured to always be on and simply placed in a conventional "sleep" mode to conserve battery life when there is no activity or alarm condition. In this situation, block 50 represents the patient taking the unit out of the "sleep" mode by pressing any of the input buttons 20, 22, or 24. Process flow then transfers to operation 52 wherein a default display screen appears on the LCD panel 26. The default display screen may contain general patient information, a menu of currently prescribed and active medications, or a listing of current pending scheduled alarm times along with the current date and time. Also on this default screen may be a query 53 asking whether additional data display is desired. If the patient does not desire additional data to be displayed, the default display remains on the LCD for a predetermined amount of time and then the component returns to the sleep mode.

If the patient wishes additional data review, the patient will push, in operation 54 the appropriate input 20, 22, or 24, whichever is indicated by the display 26. Control then transfers to the first display screen 56 which, for example, may be the first medication currently prescribed. In operation 58 the patient scrolls through the screen data until a query 60 appears. Query 60 asks whether the patient wishes to view the underlying record for a particular entry on the screen. If the patient presses the appropriate "yes" input button, control transfers to operation 62 in which the program automatically jumps to the appropriate indicated detailed record. The patient, in operation 64, may then push the appropriate "enter" button to view the detailed record. Control then transfers to operation 66 in which the patient is queried whether another record is to be viewed. If not, control then transfers back to operation 60.

If the patient wishes to view another record, control transfers to operation 68 where the patient presses the "back" button, which transfers control to operation 62 for review of another detailed record. If the patient does not wish to view a detailed record in operation 60, control transfers to operation 70 where the patient is queried whether any other data should be displayed. If not, control transfers back to operation 52 wherein the default screen is displayed for a predetermined period of time, then the component 12 returns to the sleep mode. If the patient answers the query in operation 70 in the affirmative, the "back" push button is indicated, and when pushed, transfers control back to operation 54. In this manner, the patient can review all patient accessible data programmed into the memory device 14 and loaded into the patient component 12.

As previously mentioned, the patient component 12 includes a scheduling and alarm function for the prescribed medications. The process operations which occur upon an alarm condition are shown in FIG. 5. In operation 80 the internal alarm clock in the patient component 12, when the programmed alarm time equals the current time, sounds an alarm, either visually, audibly or by vibration or a combination of these, taking the component 12 out of the "sleep" mode. Control then transfers to operation 82 wherein the particular prescription information for the precipitating medication alarm is displayed on the LCD screen. This information may be the current time, the scheduled dosage to be taken, the drug name, and possibly a description such as of the shape or color of the pill to be taken. Also, cautions may be displayed on the same screen such as —Do not take with milk—, —Take with food—, or Take only with medication Y—. Control then transfers to operation 84. In operation 84, the patient is asked whether to accept or delay action as required by the information displayed in operation 82. In the event that the patient accepts or acknowledges the action, the patient presses the input button 20, 22, or 24 that is labeled "accept" or "acknowledge" in operation 86. Control then transfers to operation 88 where the time/date and prescription medication is logged with acceptance, i.e. that the patient has taken the prescribed medication at that time. Control then transfers to operation 90 where the patient component 12 returns to the sleep mode until the next alarm condition occurs or the patient requests information as in operation 50 in FIG. 4.

However, if the patient elects to delay taking the particular medication generating the alarm condition at that time, the "delay set" labeled button is pressed in operation 92. Control then transfers to operation 94 in which the database contained on memory device 14 is queried whether it is permissible to delay. If it is permissible to delay, control transfers to operation 96 where the patient component 12 logs the time and date of this decision with the prescription information and the delay note. A revised alarm time is set and control then transfers to operation 90 where the component 12 returns to the sleep mode. If the program in operation 94 determines that delay is not permissible then the patient is allowed to reconsider. Control then transfers either back to operation 86 permitting the patient to take the medication as scheduled, i.e., the patient presses the acknowledge button, and log it appropriately or to operation 98 where the patient presses a button labeled "skip" and the failed time and date (i.e. that the patient failed to take the required dose) is logged. Control then transfers to operation 90 where the component 12 returns to the sleep mode.

The integration of the memory device 14 with this appropriate medical data in the patient component 12 can also be applied to devices that actually contain and dispense the medication. In addition, other medical assistance device adaptations for special needs such as for the hearing or sight impaired are also possible as well as a physical design for patients who are impaired from pressing buttons. In these latter instances, voice input devices may be utilized rather than buttons.

Second Embodiment

Figure 6:
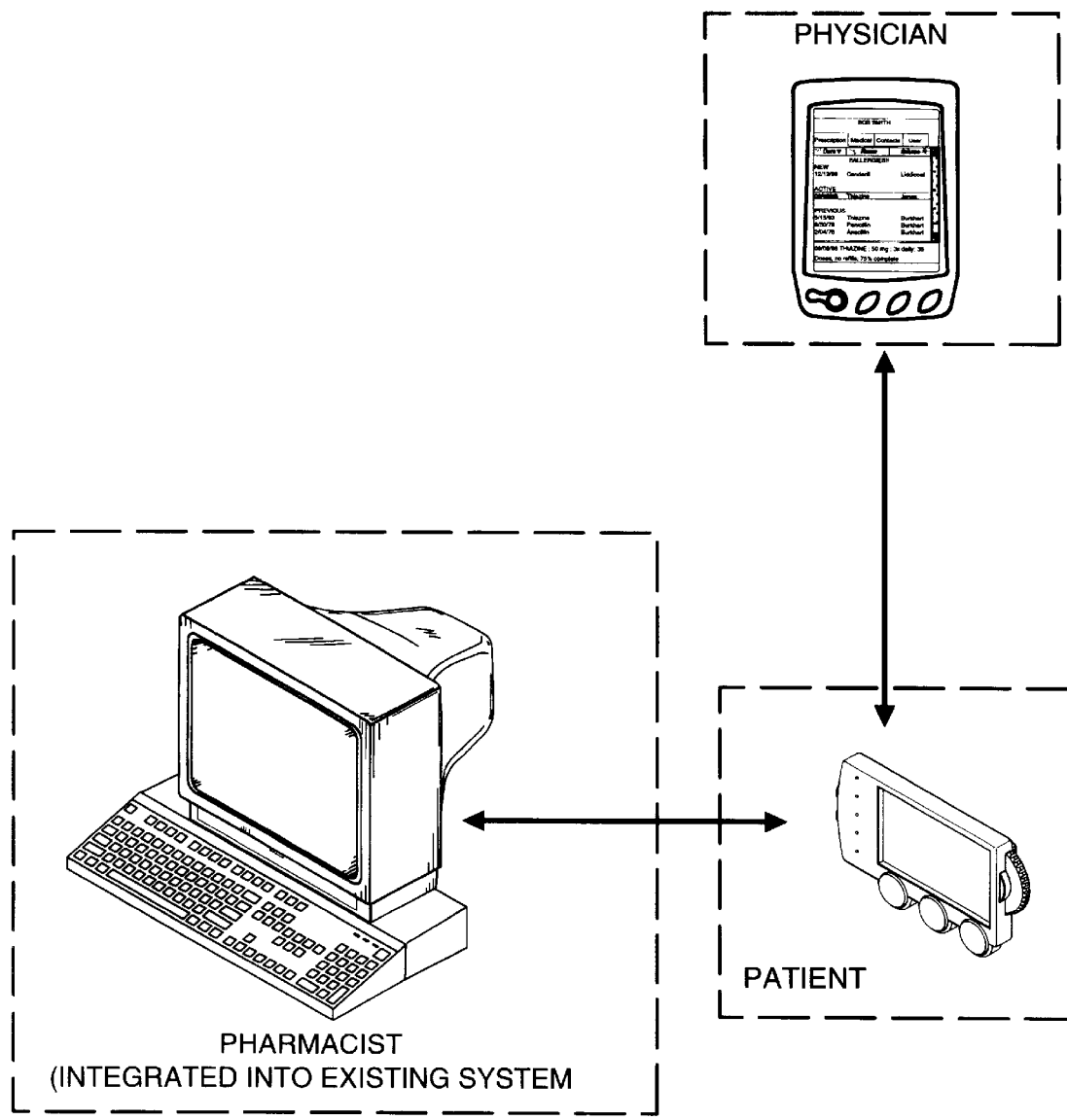
FIG. 6 is a functional system block diagram of a second embodiment of the medication management system according to the present invention.

Turning now to FIG. 6, a system 100 in accordance with a second embodiment of the invention is shown. In this embodiment, the system 100 eliminates the need for a memory device 14 as in the first embodiment. The system 100 comprises a physician's component 102, which may be embodied in a specially programmed personal digital assistant such as the Palm PC, a patient component 104, and the pharmacist component 106. The patient component 104 is linked to the physician's component 102 and pharmacist's component PC via infrared link or by cable via RS232 interface. Alternatively, the components may also be linked by modem in the situation where the patient and physician are physically separated, yet a modification of prescription is desired by the patient and approved by the physician. Thus there is no need for a smart card as all of the patient information resides in the patient component. The physician component may optionally be connected to an external storage device for archiving the data on the patient component. This optional archive capability may be alternatively provided via the pharmacist component as the pharmacist may be more accessible to the patient than the physician in many circumstances. However, it is preferred in the present invention that the patient component provide the patient with control and full information on his or her medical condition. This way, should the patient need to see a new physician or become involved in an accident, the physician and/or emergency medical personnel will have always have the necessary information in order to treat the patient appropriately.

Figure 8A:
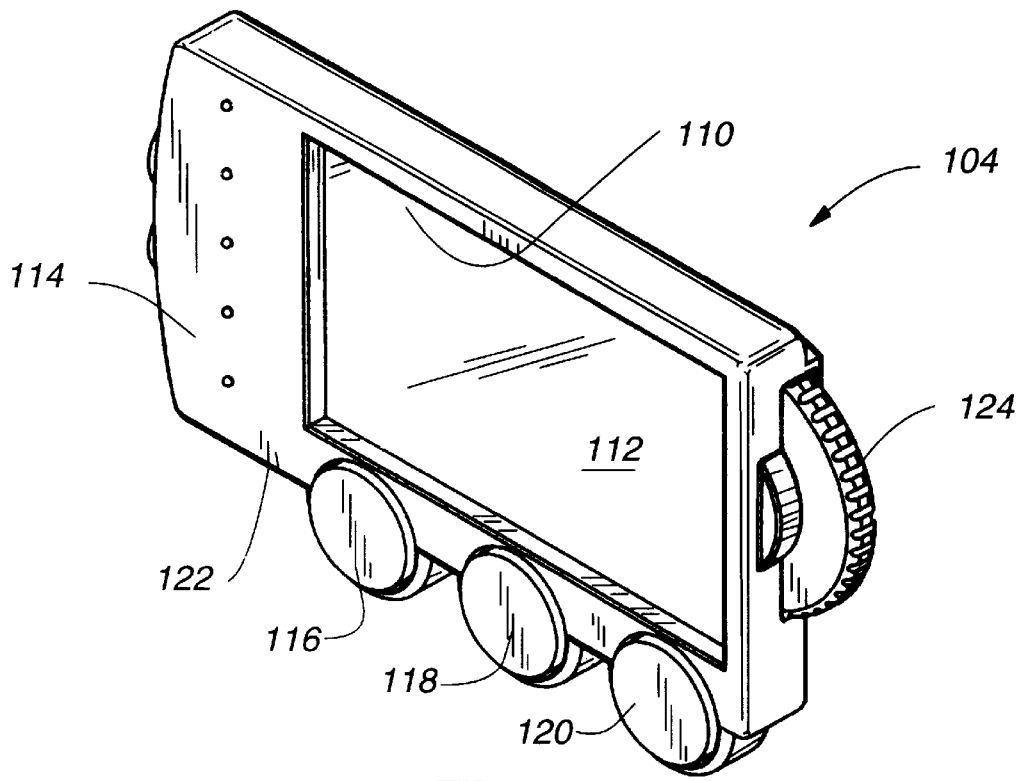
FIG. 8A and 8B are front and rear perspective views of a patient component of the system according to the present invention shown in FIG. 6.
Figure 8B:
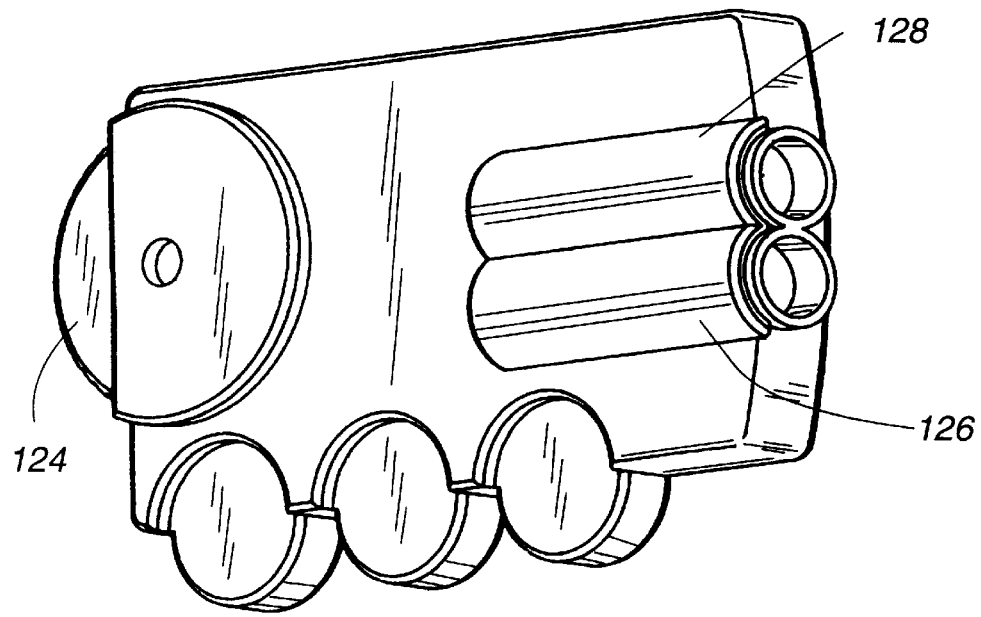

An exemplary patient component 104 is shown in front and rear perspective views in FIGS. 8A and 8B. Patient component 104 comprises a generally rectangular housing 108 that has enclosed within it a central processing unit, memory and electronic circuitry for performing the functions described herein, an alarm clock capable of scheduling and tracking a number of different prescriptions and administration frequencies, a liquid crystal display screen, a power supply, and input devices to permit the patient to interact with the component. As shown in FIG. 8A, the housing 108 includes a window 110 for the LCD screen 112 in a front side 114. A set of three push button controls 116, 118, and 120 are provided along the bottom edge 122 of the housing 108. A rotatable scroll switch 124 is mounted in the housing 108 such that an arcuate portion of the switch 124 projects from the right side of the housing 108. As can readily be seen in the rear view of the component 104 in FIG. 8B, battery compartments 126 and 128 are provided in the housing 108 for two AA size battery cells. The push button switches 116, 118, and 120 are positioned along the bottom edge of the housing 108 so that they may be actuated easily by almost any patient, especially those with limited manual dexterity. The function of each of these buttons changes as the screens on the LCD change. Consequently, the labels for the particular buttons appears in the LCD screens as shown in FIGS. 25 through 43 and as described below. The wheel 124 provided along the right side of the housing 108 is also for convenient operation by a patient's thumb. Other configurations of the patient component may alternatively be provided. The particular configuration shown in FIGS. 8A and 8B is merely one example.

Physician Component

The physician component 102 is essentially a conventional personal digital assistant such as a Palm PC with the Windows CE operating system and particularly programmed for the medication management system application. FIGS. 9 through 24 show a number of exemplary screens that take the physician through a review of the patient's medical history, contact information, and facilitate the physician's diagnosis of an ailment and assist the physician in arriving at and prescribing an appropriate treatment for the patient's ailment. Note that all names, addresses, etc. that are utilized in the description and Figures are fictional and exemplary only. Any resemblance to any person living or dead is merely coincidental.

Figure 9:
FIG. 9 is a physician component screen showing prescription information for a particular patient.

Assume that a patient, Bob Smith, comes in to a physician's office, is examined, and diagnosed with a particular illness. The physician imports data to his or her physician component 102 from the patient's patient component 104. The physician component 102 has four categories of screens as shown in FIG. 9; Prescription, Medical, Contacts, and User. The first screen that pops up is the prescription information screen for patient Bob Smith, an example of which is shown in FIG. 9. This screen shows previous prescription drugs administered to this patient as well as current, active medications, an example of which is Thiazine, prescribed by Dr. Jones. At the bottom of the screen are the particulars associated with this current prescription so that the physician knows what is being taken, how many doses have been received, as well as previous medications. At the top of the screen appears any alert conditions for this patient. In this example, the patient has allergies.

Figure 10:
FIG. 10 is a medical history screen for the patient in FIG. 9 showing recent medical history from another physician.
Figure 11:
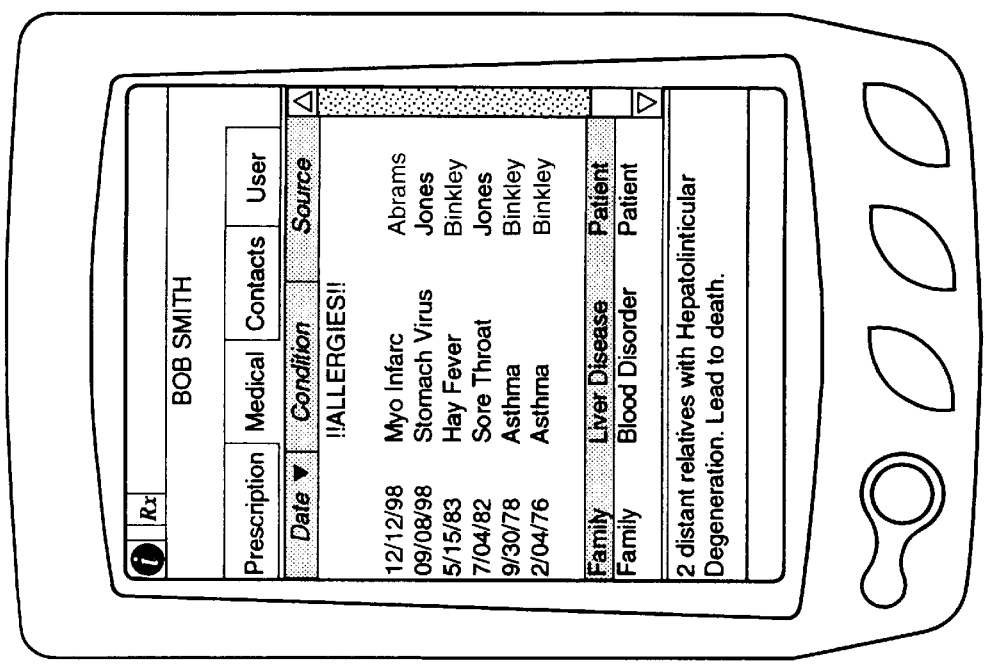
FIG. 11 is a medical history screen for the patient identified in FIG. 9 showing family medical history from the patient.

The second category of screens, Medical Information, is shown in FIGS. 10 and 11. The physician typically taps the screen image of the category to pull up the Medical Information screen as shown in FIG. 10 and taps on the medical history input from Dr. Burkhart. At the bottom of this screen is provided a short description of the illness, Influenza, treated mainly by rehydration with saline solution.

In FIG. 11, the physician has tapped on one of the family history entries provided by the patient in FIG. 10 and on the liver disease entry on FIG. 11 to display the information that 2 distant relatives had hepatolinticular degeneration. Thus the data uploaded from the patient component 104 not only includes prescription history but also medical history provided both by physicians and by the patient.

Figure 12:
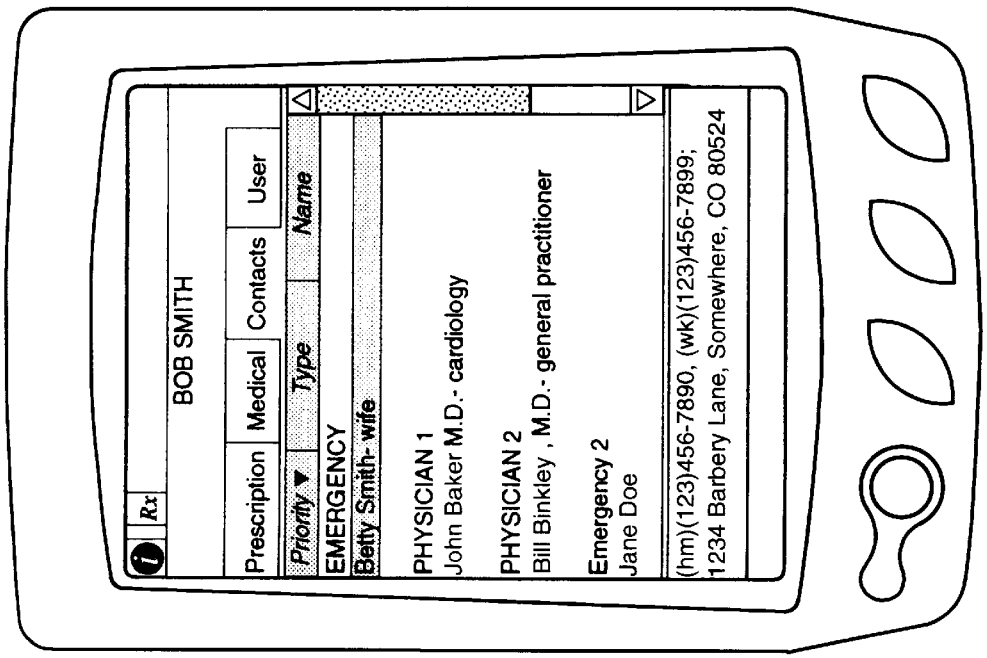
FIG. 12 is a contact screen for the patient identified in FIG. 9 showing next of kin contact information.
Figure 14:
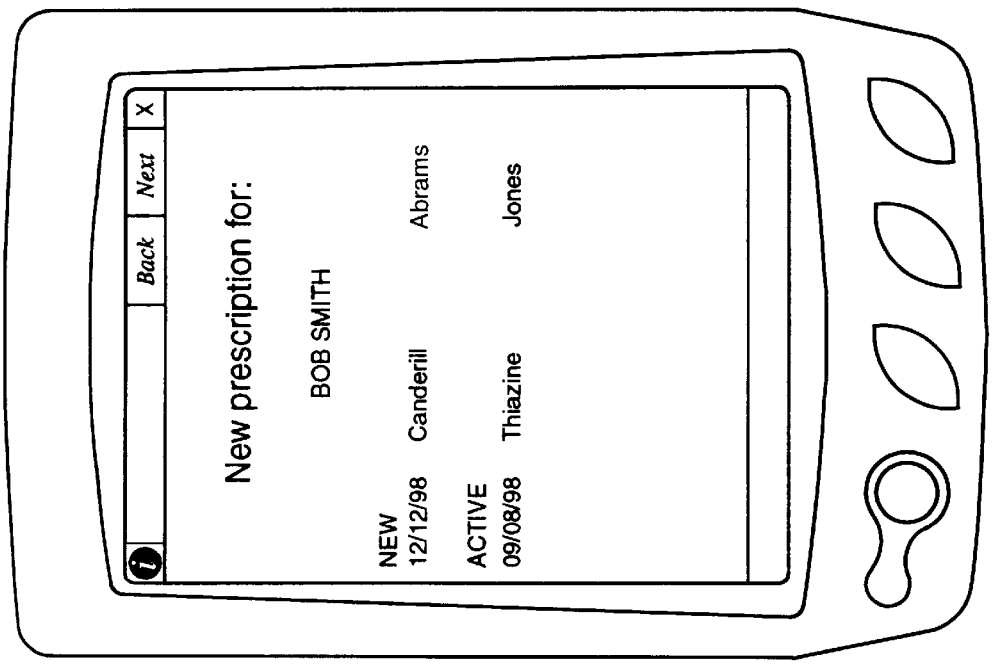
FIG. 14 is a current prescription screen for the patient identified in FIG. 9.

FIG. 12 illustrates the Contact screen for patient Bob Smith. The physician has tapped on the patient's wife's emergency contact entry, and her contact information such as telephone numbers and address are shown below the list of contacts.

Figure 13:
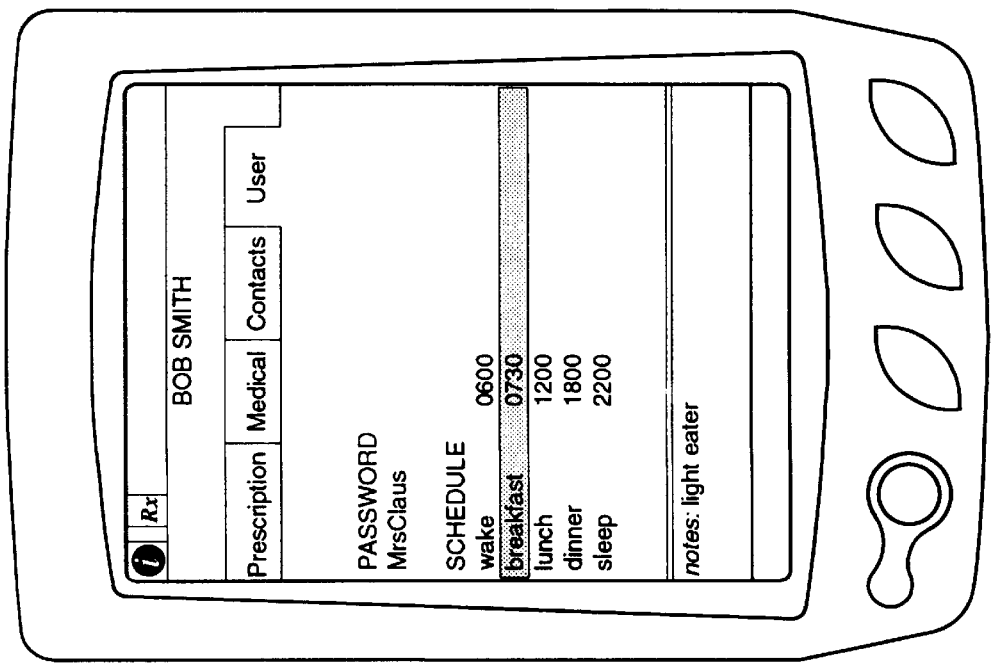
FIG. 13 is a user screen for the patient identified in FIG. 9 showing Bob Smith's normal daily routines and any particular notes.
Figure 16:
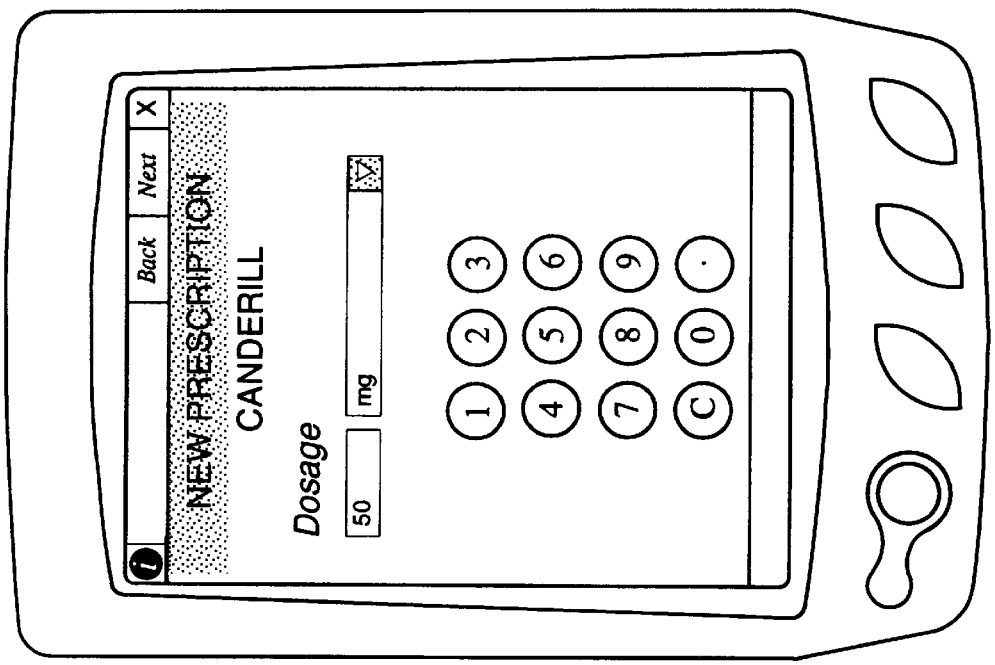
FIG. 16 is a physician's new prescription dosage screen for the drug identified in FIG. 15.

FIG. 13 illustrates the patient's user information such as his password for accessing and changing personal protected information that the patient does not want to be accessible by anyone but the physician, and habitual schedule information. This information will be considered by the scheduling program embedded in the patient component in order to optimally schedule the administration of medications in accordance with the patient's general activity patterns. For example, Bob Smith awakens at 0600 and eats dinner at 1800 or 6 pm. Therefore if a prescription requires a medication to be administered twice daily, and does not require food to be taken at the same time, the program would schedule the drug to be taken at 0600 and 1800 rather than midnight and noon. If the drug must also be taken with meals, the program would then schedule the drug to be taken at 0730 and 1800 so as to be as close to 12 hours apart as possible but still at a meal. Thus the information provided on the user screen as shown in FIG. 13 is an important consideration in the software scheduling of drug administration.

Figure 15:
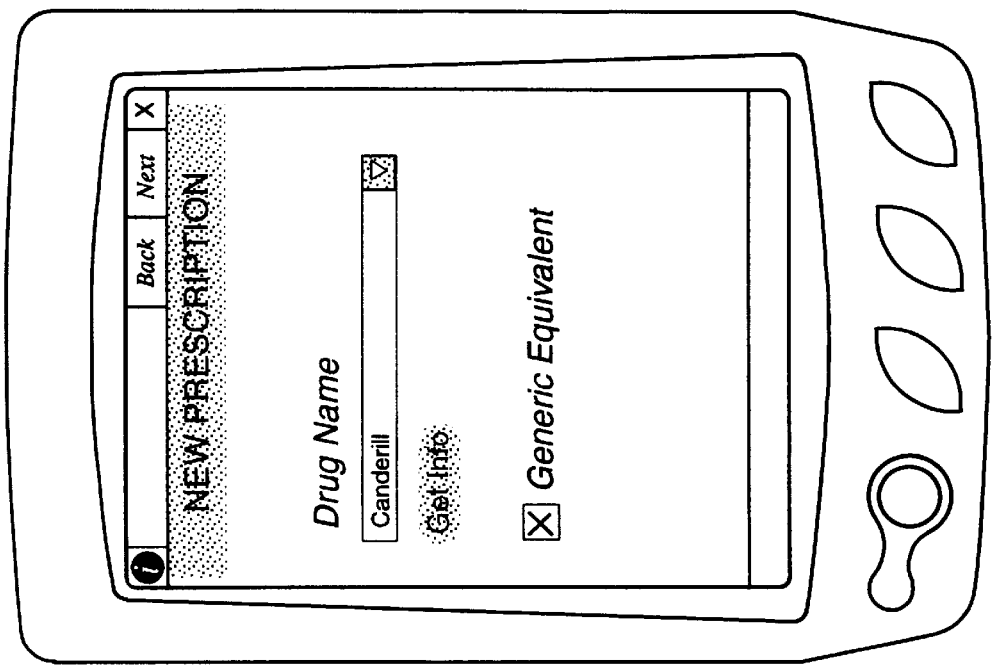
FIG. 15 is a physician's new prescription drug screen.
Figure 17:
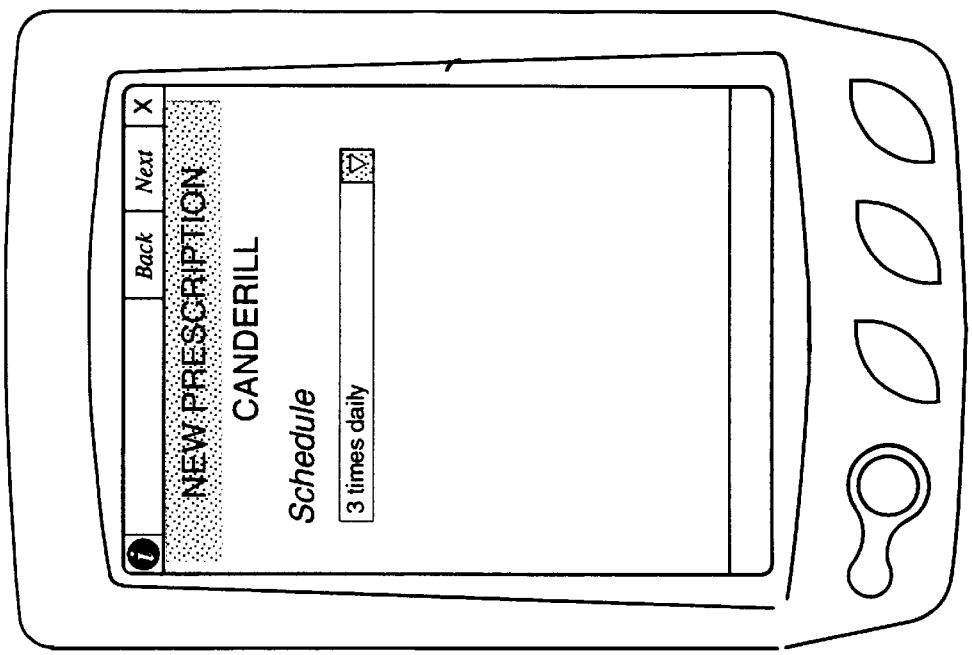
FIG. 17 is a physician's new prescription schedule screen for the drug identified in FIG. 15.

The screens shown in FIGS. 14 through 24 illustrate how the system in accordance with the present invention assists the physician in prescribing medication to a patient. Assuming that the physician, Dr. Abrams in this example, decides to prescribe a new medication for patient Bob Jones as shown on the screen in FIG. 14. The sequence begins in FIG. 15 with the physician tapping on "NEW" back in FIG. 14. FIG. 15 pops into view. Here, the physician component shows a list of drugs via a pull down menu. The physician selects and taps on the desired medication, in this case, Canderill and taps on Generic Equivalent. The physician then taps on "Get Info" and the screen of FIG. 16 pops up. The physician can enter manually via the on screen keypad the desired dosage of Canderill, or alternatively select the available commercial dosage via a pull down menu in FIG. 16. After selecting or inputting the desired dosage, the physician taps "next" at the top of the screen and the screen shifts to the schedule screen as shown in FIG. 17. Here the physician can select the frequency of medication from a pull down menu.

Figure 18:
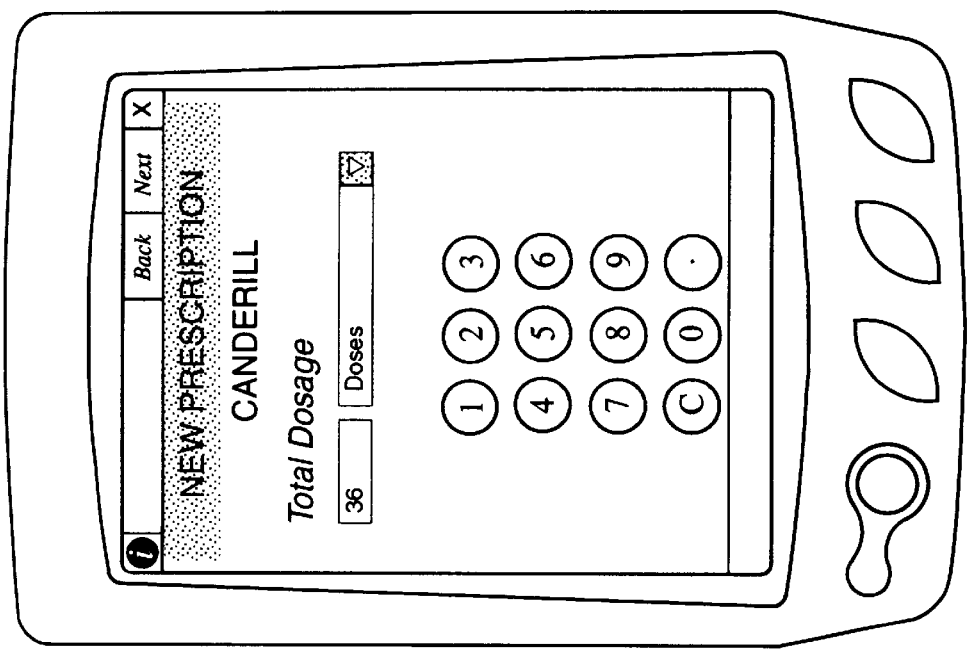
FIG. 18 is a physician's new prescription total dosage screen for the drug identified in FIG. 15.

Once the schedule is selected, the physician taps on "next" and the screen automatically shifts to the total dosage screen, FIG. 18, where the physician selects the number of doses, milliliters, ounces, etc. that may be required for the particular medication. Again, a keypad is provided on screen for the physician to numerically enter the number of doses required.

Figure 20:
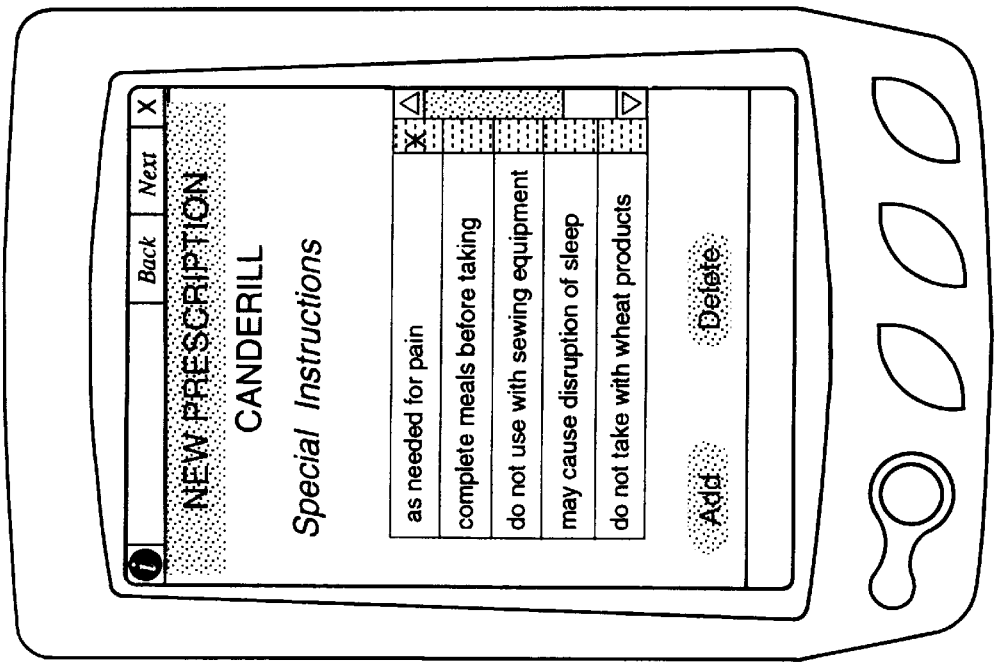
FIG. 20 is the physician's new prescription special instructions screen for the drug identified in FIG. 15 with a pull down menu expanded.
Figure 19:
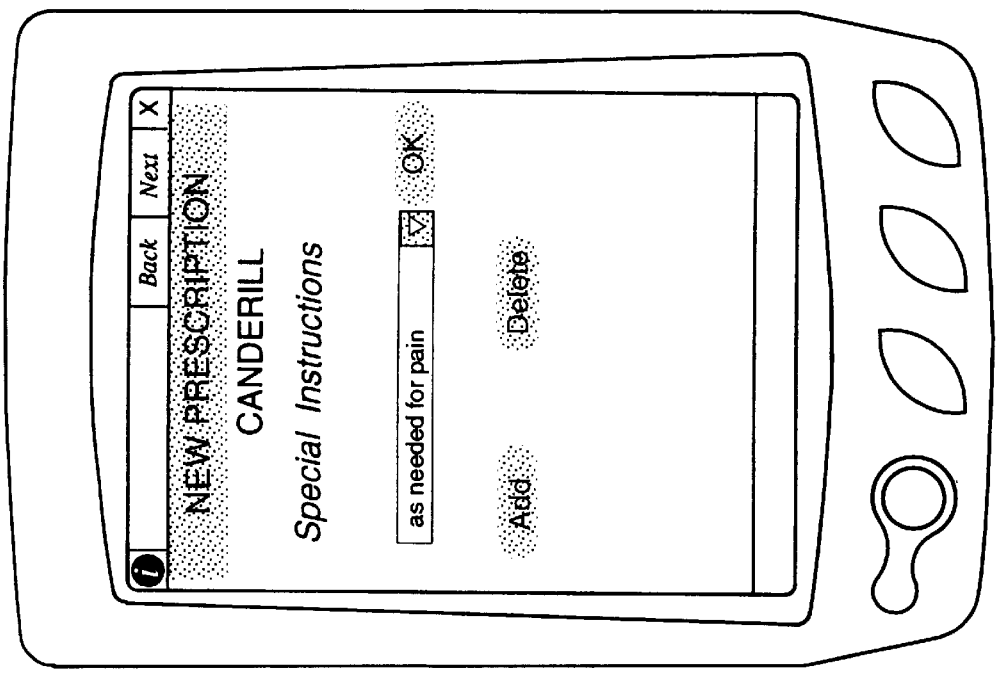
FIG. 19 is a physician's new prescription special instructions screen for the drug identified in FIG. 15.
Figure 22:
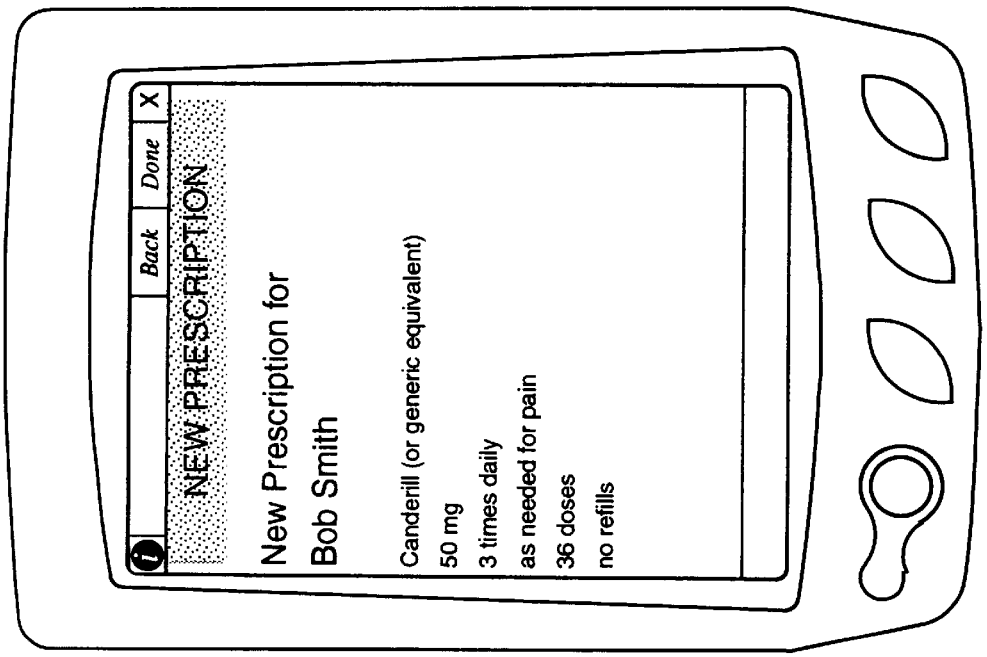
FIG. 22 is the physician's summary new prescription screen for the drug identified in FIG. 15.

When the total dosage has been selected the physician taps on "next" at the top and the screen automatically shifts to that shown in FIG. 19 where special instructions may be selected from a pull down menu or manually entered. If the latter is the case, the physician taps on "add" and a miniature keyboard appears which the physician can utilize to add a customized entry. This entry will then be added to the database and the component may be directed to subsequently show this entry as a selectable option from the pull down list of special instructions as is shown in FIG. 20.

Figure 21:
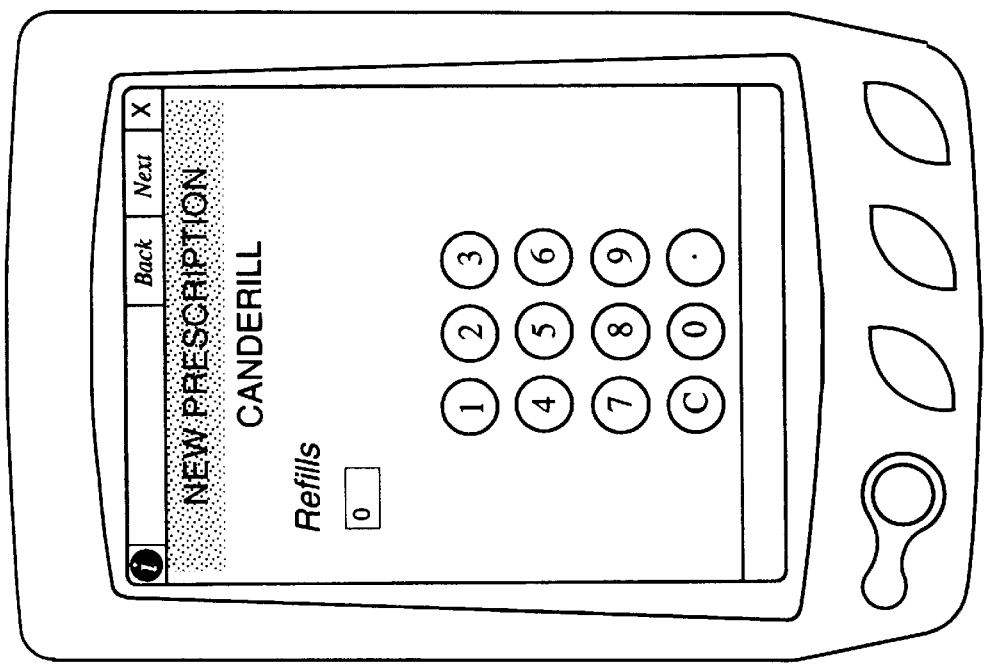
FIG. 21 is the physician's new prescription refill instruction screen for the drug identified in FIG. 15.
Figure 24:
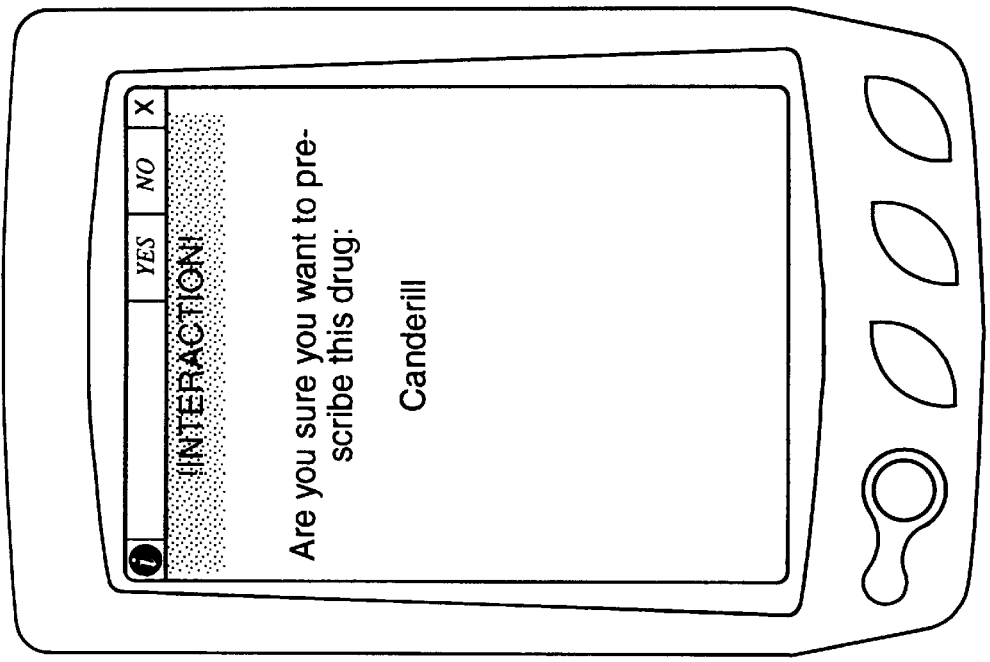
FIG. 24 is an exemplary potential interaction screen for the drug identified in FIG. 15.

When special instructions, if any, have been entered, the physician taps on "next" and the screen shifts to the Refills screen shown in FIG. 21. Here the physician enters the number of refills of the prescription that may be obtained from the pharmacist. The physician then taps again on "next" and the screen then shifts to a summary of the new prescription shown in FIG. 22. If this new prescription is satisfactory, the physician taps on "Done" at the top of the screen. Alternatively, if the physician wants to modify the prescription, he can tap on "Back" to go to the desired screen to change the prescription in whatever manner he chooses.

If the physician taps on "Done" then the processor queries a database resident in the physician component 102 for cautions and interactions. If there are any cautions, they are shown as in FIG. 23 along with a "Cancel" or "Prescribe" query. If the physician chooses "Prescribe", then any interactions in the caution screen will trigger a confirmation screen shown in FIG. 24. If the physician chooses "yes" on this screen, then the prescription is added to the patient database for Bob Smith and downloaded to Bob Smith's patient component 104 along with a confirmation security code of the prescribing physician.

The patient then takes the patient component to the pharmacist who then transfers the patient data from the patient component 104 to the pharmacist's PC component 106 for execution of the prescription. The pharmacist may then fill the prescription after the pharmacist's component verifies the authenticity of the prescription uploaded from the patient component. This system can completely replace the current conventional practice of hard copy prescriptions by the physician. Alternatively the system may supplement the paper prescription in that the pharmacist simply augments the physician provided data downloaded from the physician component to the patient component.

The pharmacist component 106 in particular augments the information provided to the patient component by adding more up to date administration cautions and instructions to the patient component that normally are provided in small print today along with most prescriptions as they are filled. These instructions may include such things as not to take the medication with alcohol, don't take more than three days in a row, etc. In addition, the pharmacist component may flag additional potential drug interactions that may have been more recently identified as pertinent by the medical and pharmaceutical community.

Potential interactions may be detected by the physician component 102. Identified cautions or potential interactions flagged by the software routine in the Physician component are displayed to the physician prior to confirmation of the prescription as exemplified by the screen in FIG. 23.

Similarly, a check of potential interactions and cautions concerning a particular prescription is performed in the pharmacist component 106. If an interaction is detected by the physician or pharmacist software, it warns the pharmacist or physician of the severity of the interaction. The interaction check in the pharmacist's computer and in the physician's component 102 serves a watchdog function only. The pharmacist or physician have the ability to override the software warning and prescribe the drug anyway. This is routinely done by physicians today for minor potential interactions when substitute drugs are either unavailable or would cause even more severe interactions. In either case, the interaction is flagged in the patient component 104 such that the patient can review the interaction warning thus alerting the patient that there is an interaction potential between two drugs. The patient is then able to read about the interaction, usually in a brief form, and consult the physician or pharmacist for more information if clarifications are needed. This capability in the patient component 104 permits the patient to make the most informed decision possible about his or her medication and/or medication schedule.

The potential drug interactions primarily become extremely important in situations where a patient needs to manage a large number of medications simultaneously. For example an HIV positive individual may take several drugs simultaneously or in a prescribed sequence. Anti-HIV drugs often have 10–20 known interactions each. Some drug families interact with whole families of other drugs. Consequently, strict scheduling and sequencing of some of these drugs may be particularly important for optimized patient care.

Currently there is little general interaction data available concerning potential interactions between drugs when doses are delayed or skipped. However, the physician may provide, through the physician component 102, specific instructions to the patient in these cases. This information may appear as separate potential interaction warnings or may actually be introduced into the patient component scheduler software so as to pop up if the patient attempts to postpone, delay or skip medication doses. The patient component will track and monitor a patient's track record for taking medications. Assuming that the patient accurately records medications consumed on the patient component, via requested responses, when medication is administered, the patient component data may be helpful to the prescribing physician in determining the effectiveness of a particular line of treatment. This data, for experimental drugs, may also prove extremely valuable to drug companies as well as the physicians in determining whether a drug regimen is or is not successful.

Figure 44:
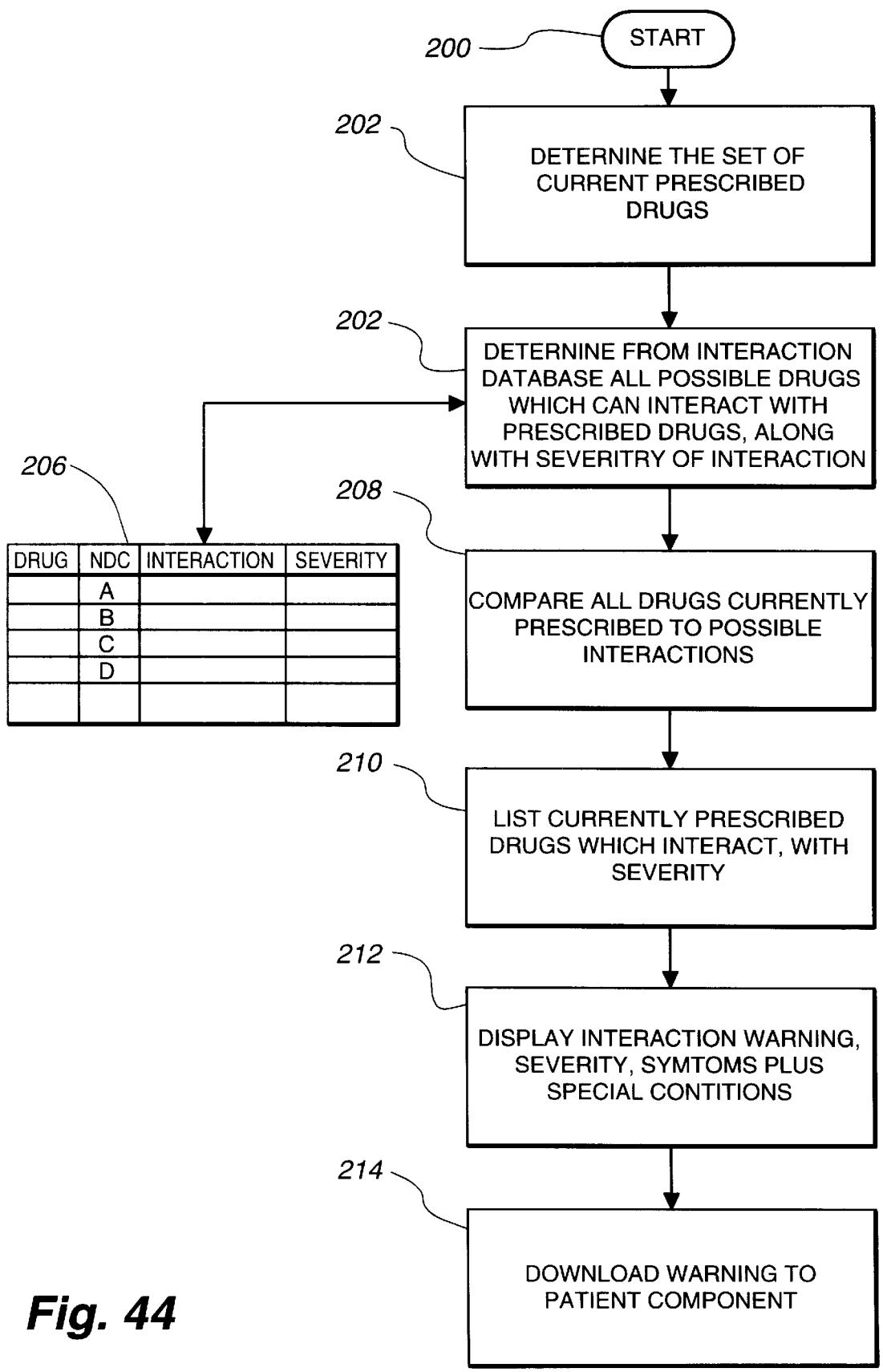

The potential drug interaction software routine utilized by the physician component 102 and/or the pharmacist component 106 is shown generally in FIG. 44. This software routine may also be provided in the patient component 104 or a simplified version provided in the patient component 104. In the latter case, the routine may operate on a database contained in the patient component 104 or may optionally be capable of tapping into a large mainframe database via modem and internet connection. This latter capability may be optimally utilized when the patient desires to include OTC medication information in the patient component 104 as the potential interactions for OTC drugs may be extensive compared to the individually prescribed prescription drugs prescribed to the patient.

The pharmacist component 106 may also be utilized to provide patient prescription information to and from the covering insurance organization. In addition, as will be shown below, the patient, while self administering the medication, may identify and document interactions or side effects that can automatically be updated to the medical community through the pharmacist component. This latter feature may be particularly valuable for experimental drugs utilized on a trial basis.

Figure 7:
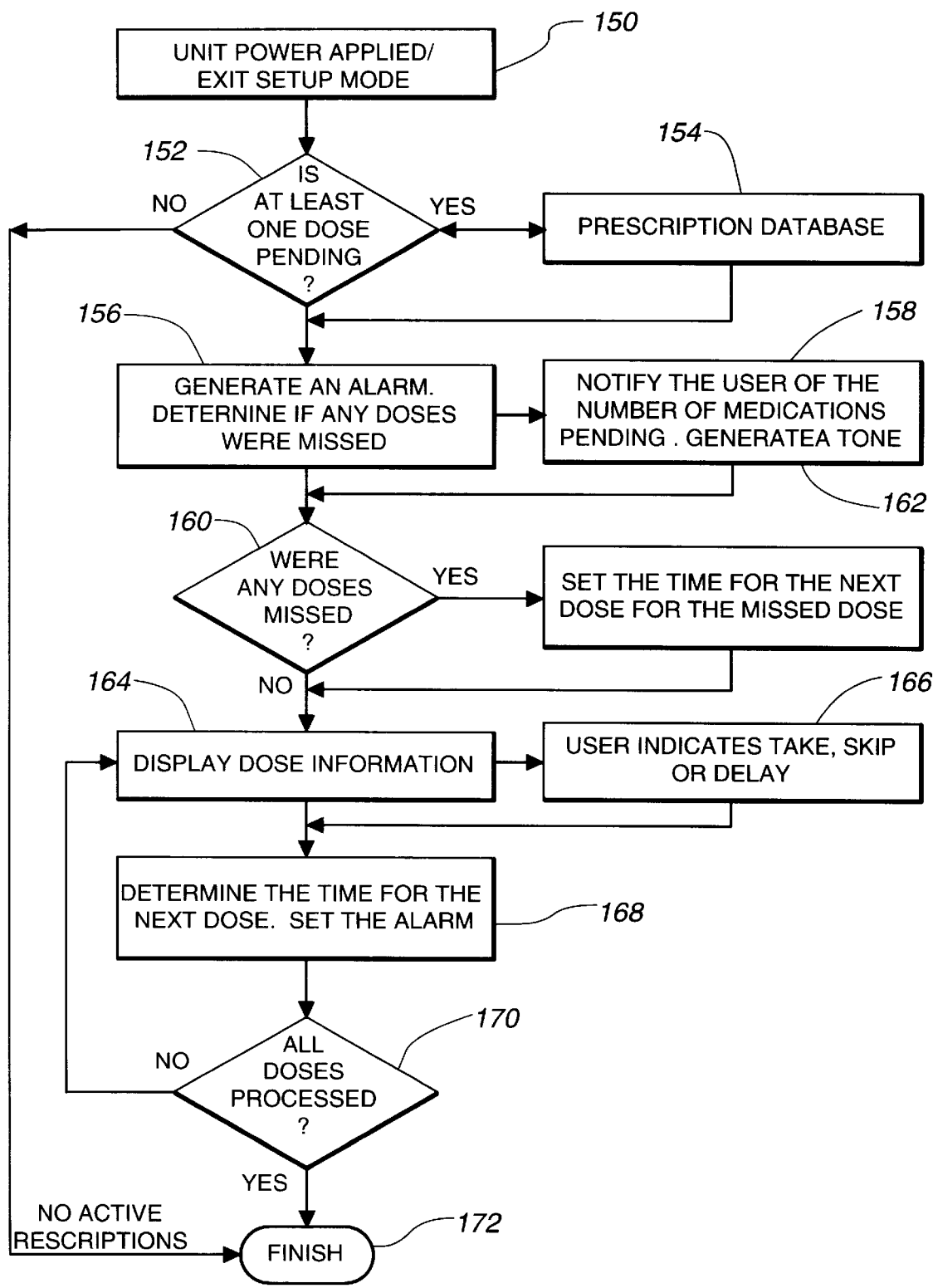
FIG. 7 is a flow diagram of a software scheduling example in the patient component in accordance with the medication management system shown in FIG. 6.

FIG. 7 shows a flow diagram of the scheduler software utilized in the patient component 104. As in the first embodiment 10 described above, the component 104 stays in a "sleep" mode to minimize power drain. In the sleep mode, only the alarm clock continues to operate. Upon generation of an alarm by the clock, or by the patient pressing any one of the three buttons 116, 118, or 120, power is applied to the patient component 104 in operation 150 and the LCD screen lights up and adjusts for optimum contrast depending on the ambient light conditions. The processor is then queried in operation 152 whether there is at least one dose pending. If yes, then the processor queries the prescription database 154 within the patient component 104.

Every active prescription has a time and date tag indicating when the next dose is to be taken. The current time and date are compared to the time and date tag for each active prescription in the component's database. Pending doses are those having time and date tags equal to or less than the current time and date. If there is at least one dose pending, control transfers to operation 156 where an alarm is generated. The patient component counts the number of medications having pending doses. Prescription time date tags are compared to the current time and date. If the difference in time between when the prescription should have been taken and the current time is greater than the allowable variance which is stored in the prescription information, the dose is logged as having been missed.

Missed medications are logged for each time that they were missed. A medication which is not taken within its allowable window is rescheduled for its next dose as if it were taken or skipped. This is to prevent doses from being taken too close together. The user will be prompted later to indicate whether missed doses were taken or skipped.

Once an alarm condition is generated in operation 156, a tone or other indication of the alarm is activated in operation 158. The patient component 104 then displays the number of medications pending. Control then transfers to operation 160. The processor determines if any doses were missed in operation 160. If yes, control transfers to operation 162 where the time and date tag for the medication dose is set for the next dose for the missed medication. Control then transfers to operation 164.

If the answer in operation 160 is no, control transfers directly to operation 164 where the alarming dose information is displayed on the screen of the patient component 104. The patient then selects, in operation 166, whether to take, skip, or delay administration of the medication. Control then transfers to operation 168 where the time for the next dose is computed and tagged and the alarm set accordingly. Control then transfers to operation 170 which queries whether all doses pending have been processed. If so, control transfers to operation 172 where the patient component returns to the sleep mode, awaiting the next alarm condition. If the answer to the query in operation 170 is no, then control transfers to operation 164 to display dose information for the next pending medication.

If the answer to the pending dose query in operation 152 above is no, signifying there are no doses pending, operation transfers directly to operation 172 where, after a predetermined period of time, the patient component 104 returns to the sleep mode.

The time for the next dose for each active medication is calculated by adding the dosage interval to the current time. Doses which are delayed are postponed for ½ hour. Skipped doses are logged as missed, and the next dose alarm is set for the next interval as if the scheduled had been taken. The interval between doses is calculated depending on the requirements of the specific prescription. Dose intervals can be set as a fixed number of hours, or as a number of doses during each daily period. The interval would then be calculated by dividing the daily period by the number of doses to be taken each day. The daily period for each dose is determined as either the period of time during which the patient is awake, or 24 hours if the prescription must be taken on a regular basis, even if the patient is normally asleep. Additionally, the interval may be specified as occurring at a number of fixed times each day, such as the times when the user eats regular meals. The patient's schedule is entered by the patient and includes wake time, bed time, and the times of each regular meal (breakfast, lunch and dinner). Doses may be scheduled to occur on the patient's schedule, or relative to the schedule. For example, a dose might be scheduled to be taken with lunch, or within ½ hour before of after lunch. Each time that a dosage is taken, the number of remaining doses is decremented. If no doses remain, the prescription is finished, the medication is removed from the pending dosage registers, and no additional alarms will be generated for that prescription.

Figure 25:
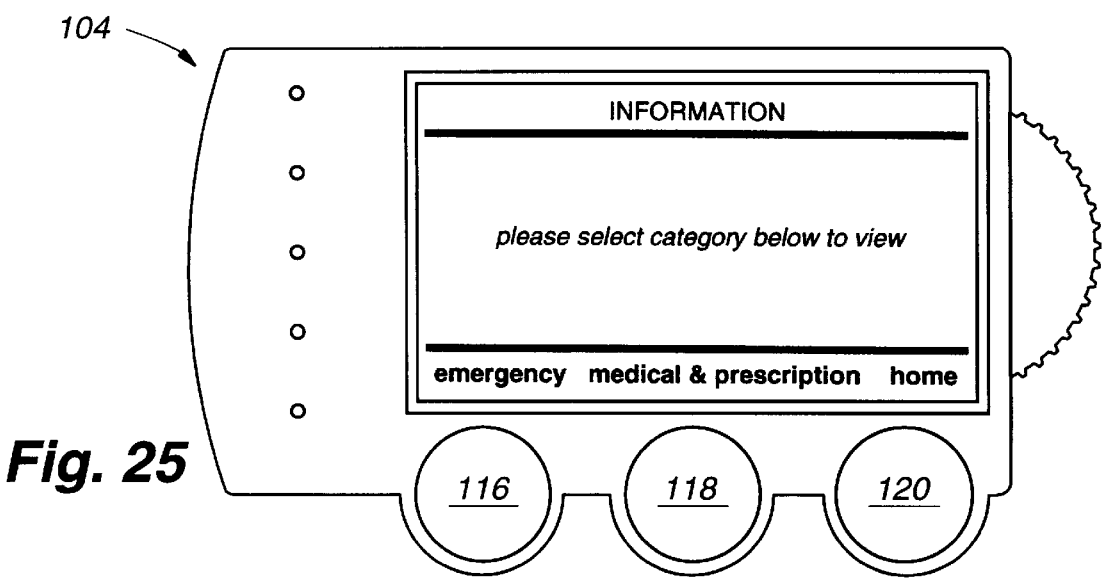
Figure 26:
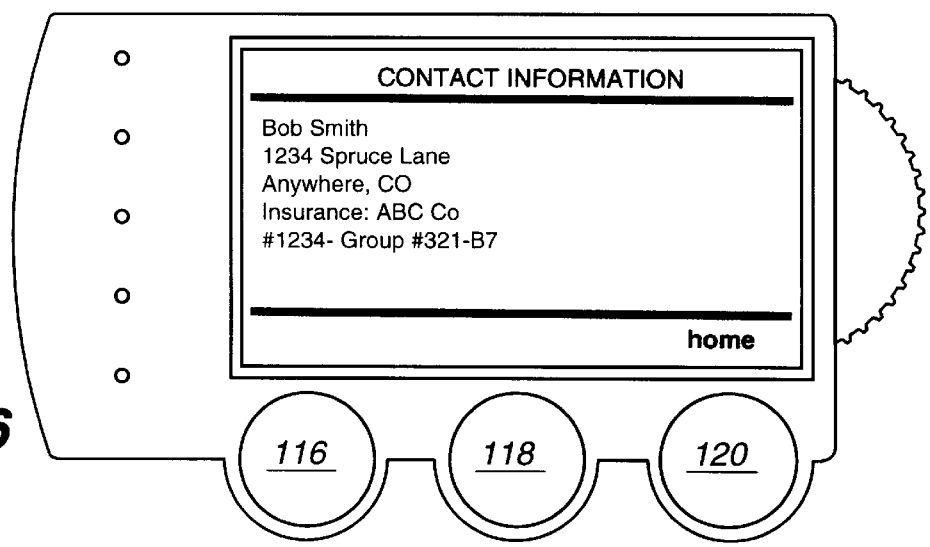

FIGS. 25 through 43 show exemplary information displayed on and controlled by the patient component 104. In FIG. 25, a patient has pressed one of the buttons 116, 118 or 120. The unit powers out of the sleep mode and a default screen is shown, requesting the patient to select one of the three options shown: emergency information, medical and prescription information, or home information FIG. 26 shows the information typically displayed upon the patient selection of button 120. The information includes the patient's name, address, and insurance information.

Figure 27:
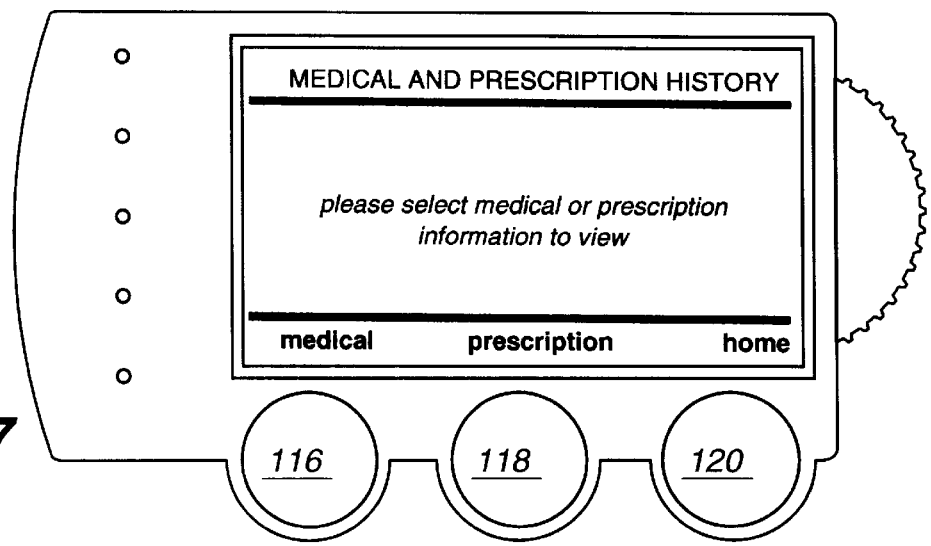

FIG. 27 shows the information displayed upon the patient selection of button 118 in FIG. 25. This is a preliminary medical screen permitting the patient to select between medical or prescription information.

Figure 28:
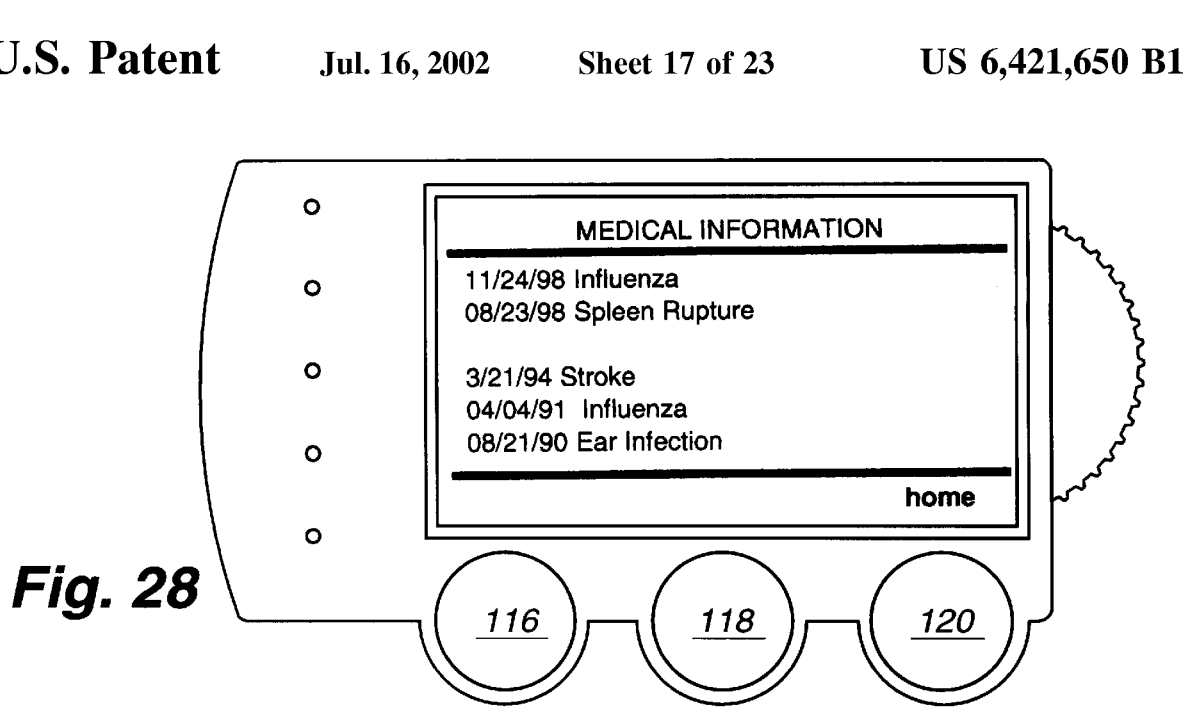

FIG. 28 shows the information displayed when the medical button 116 is pressed. It is a reverse chronological listing of medical conditions which have been entered in the patient database.

Figure 29:
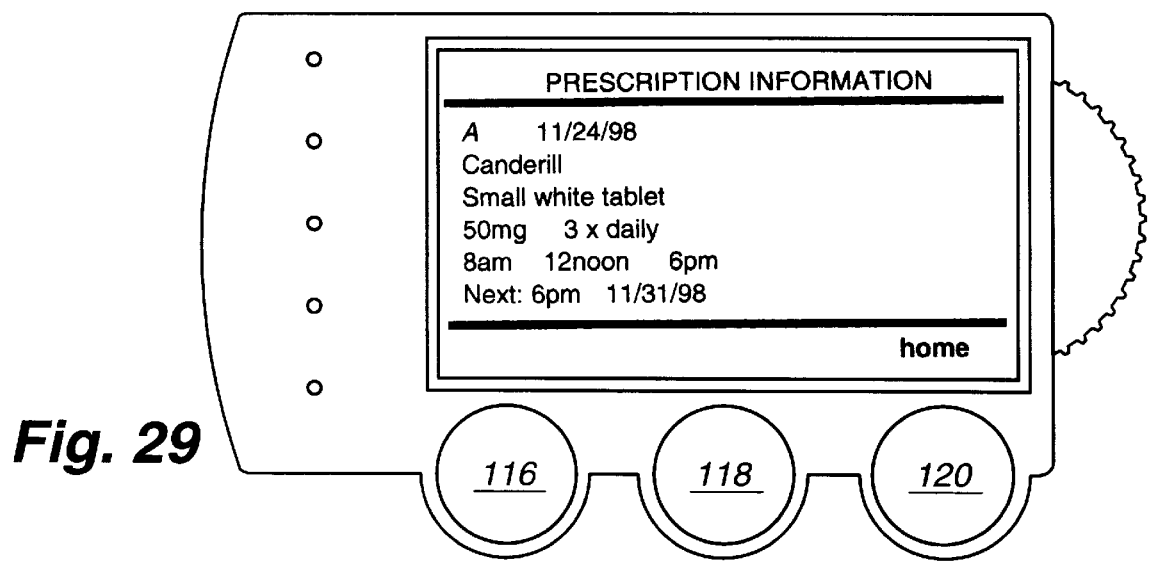

FIG. 29 shows the information displayed when the prescription button 118 is pressed. Again, a reverse chronological listing of prescriptions is displayed, setting forth the name of the drug, the dosage and frequency, a physical description of the drug such as a small white pill, the schedule, and when the next dose is presently scheduled to be administered.

Figure 30:
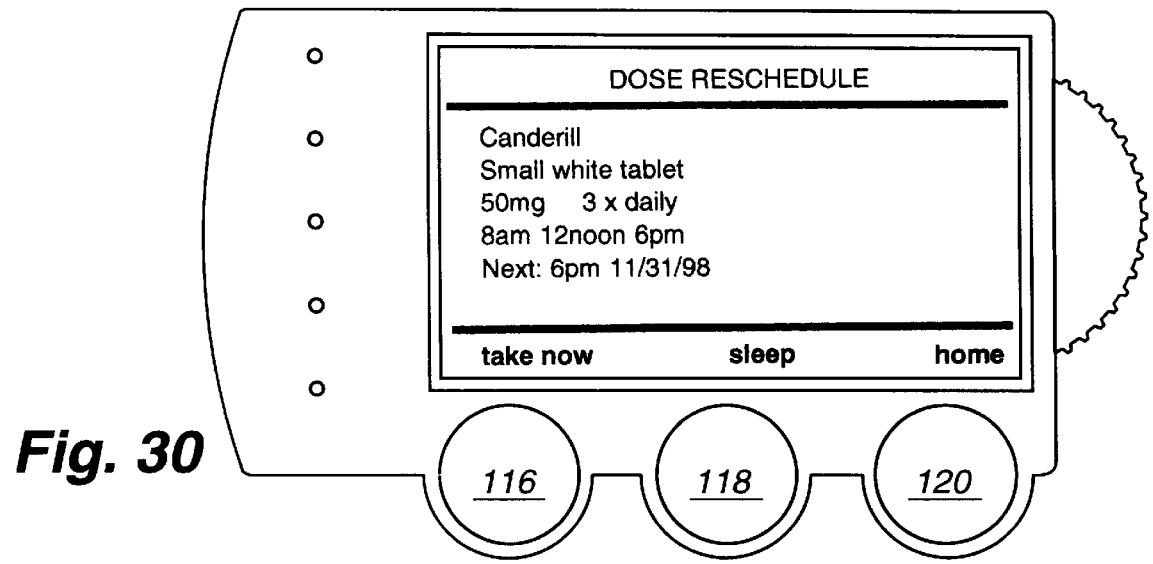
Figure 31:
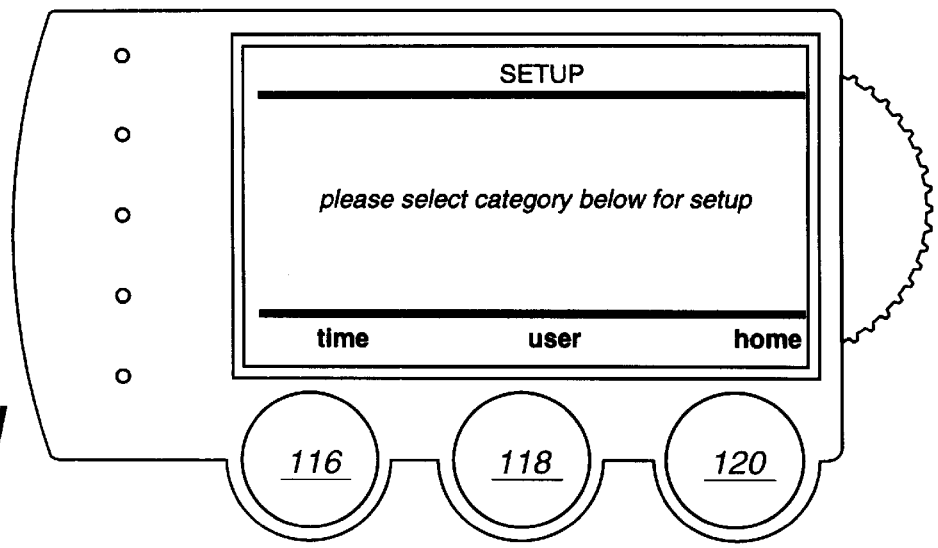

FIG. 30 shows the screen information when an alarm condition is activated. The display shows the drug name, physical description, dosage and frequency and schedule. Note that the three buttons 116, 118, and 120 now are labeled "take now", "sleep" and home.

FIGS. 31, 32, 33, 34, and 35 are self explanatory. These screens show setup information for setting the clock, password and personal schedule information.

Figure 36:
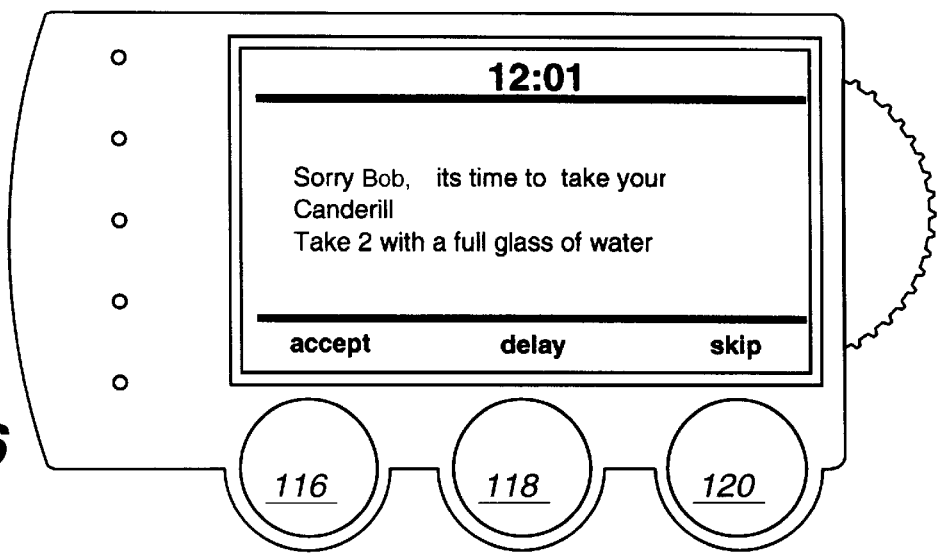

FIG. 36 refers back to FIG. 30 where an alarm condition has been activated. If the scheduling program determines that the medication cannot be delayed, because of other drug interactions or otherwise, the screen will continue to instruct the patient to take the medication now, i.e. press the accept button 116. When the instruction is accepted, the time and date is logged and the next dose administration is displayed as in FIG. 37. Alternatively, if the dosage scheduled in FIG. 36 may be skipped but not delayed, the patient presses the skip button 120 in FIG. 36 and the processor transfers to the screen shown in FIG. 38, and the skipped dosage is logged. Finally, if delay of administration of the dosage was permissible in FIG. 36, the delay is logged and the alarm reset for thirty minutes later. After two delay periods, the screen will be as shown in FIG. 39 if the medication is taken at that time.

Figure 37:
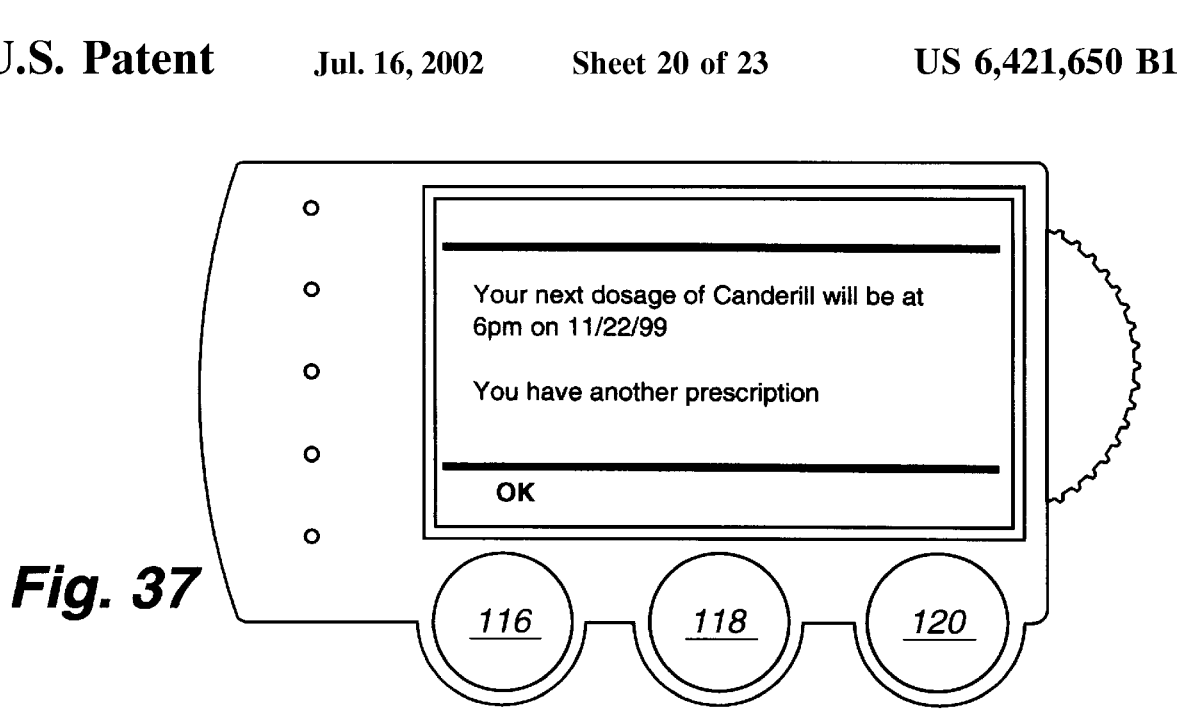
Figure 38:
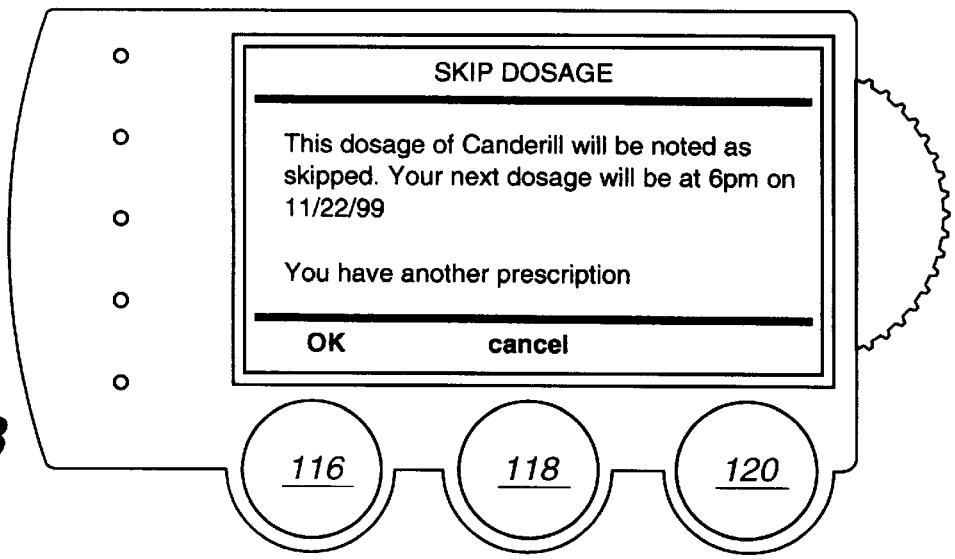
Figure 39:
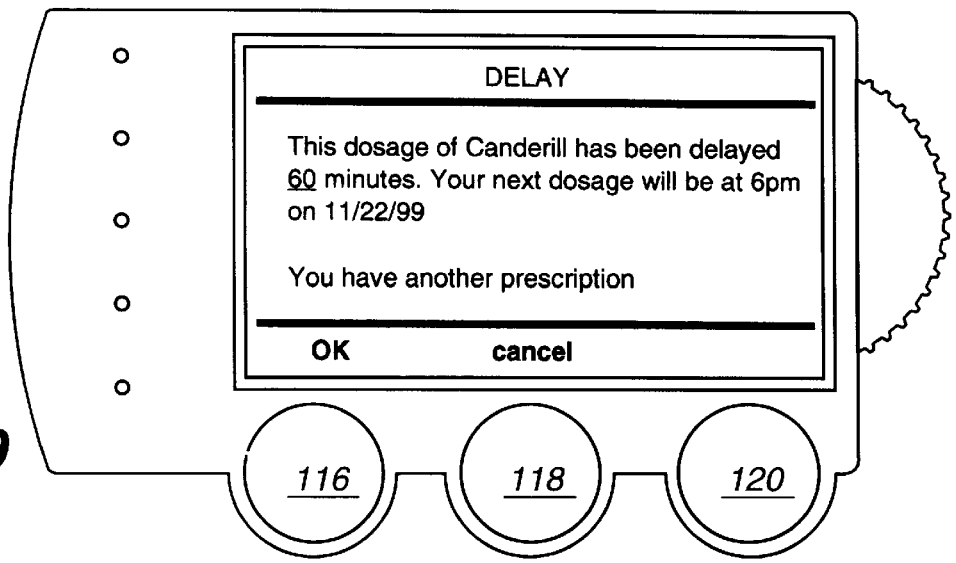
Figure 43:
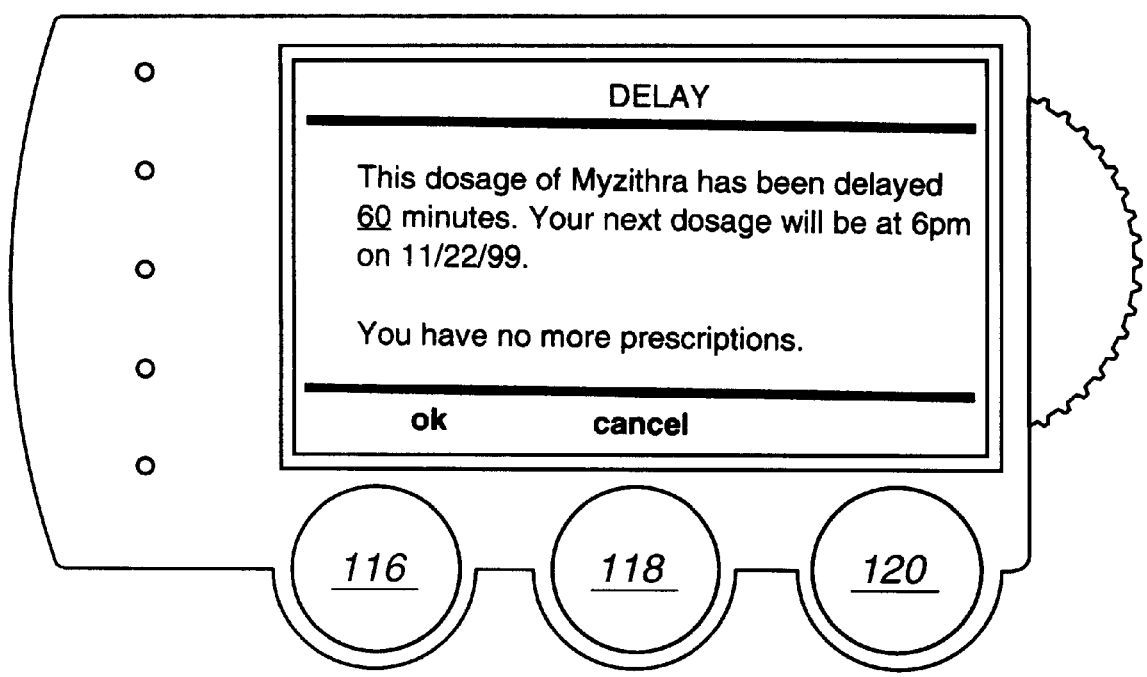

FIGS. 37 through 39 indicate that there is another drug that must be administered. After selecting OK in FIGS. 37, 38, or 39, the next drug is displayed as shown by example in FIG. 40. The process of proceeding through the screens is then repeated. For example, FIG. 41 shows the screen which appears if "accept" is chosen in FIG. 40. FIG. 42 shows the screen which appears if "skip" is chosen in FIG. 40. FIG. 43 shows the screen which appears of "delay" is chosen in FIG. 40.

A unique feature of the management system 10 and 100 in accordance with the present invention is the capability for identification, evaluation and flagging of potential adverse interactions between prescribed drugs to each of the three parties to the medication administration triangle, the physician, the pharmacist, and the patient. FIG. 44 is a simplified flow diagram of the drug interaction identification process according to one embodiment of the present invention. In the following description, the steps shown in FIG. 44 may preferably be performed by the physician component 102 and/or the pharmacist component 106. The results may be downloaded into the patient component in accordance with the physician's or pharmacist's discretion.

Figure 23:
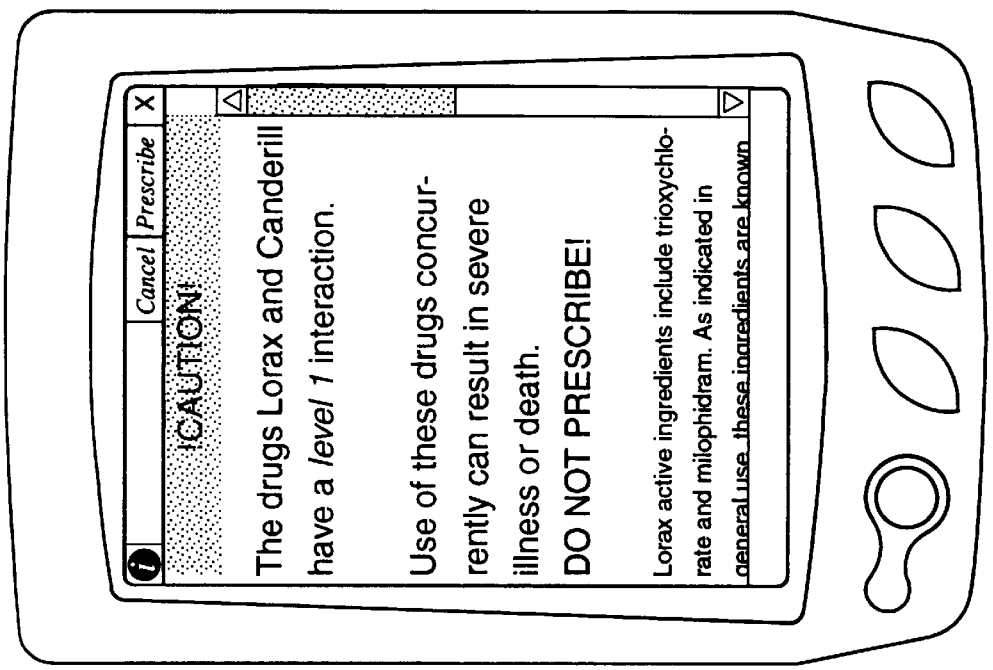
FIG. 23 is an exemplary caution screen for the drug identified in FIG. 15.

The present system is envisioned as including relational database tables of drugs in a relational database such as Microsoft Access which includes the drug names, their National Drug Code (NDC) numbers, an interaction identifier, and a severity of interaction indicator for each identified interaction. For example, as is shown in FIG. 23, the drug Canderill is displayed as having a level 1 severity interaction with Lorax. The severity levels are envisioned as ranging from 1 to 5, with 1 being mild and 5 being deadly. As is shown in FIG. 23, level 1 severity is not absolutely mild. The concurrent use of these medications together can result in severe illness or death. However, the assignment of level 1 indicates that generally the interaction is of mild severity.

Referring now to FIG. 44, an exemplary interaction query begins in block 200 when the patient component interfaces with the pharmacist component in filling a prescription or when the physician component is used to prescribe a new drug to a patient whose patient component is coupled to the physician component as described above. In operation 202 the set of currently prescribed drugs is obtained by the program from the patient component memory device. The program then jumps to operation 204 wherein the drug database 206, accessible via the pharmacist's computer or resident in the physician component, is queried to determine all possible drugs which can interact with the set of prescribed drugs identified in operation 202. This set of possible drugs, along with their severity level of interactions, are then compared with the drugs currently prescribed to identify any possible interactions between the prescribed drugs in operation 208, Control then transfers to operation 210 where the currently prescribed drugs which interact, with their severity levels, are identified. Control then transfers to operation 212 where the interactions are sequentially displayed for the pharmacist or physician, along with their severities, symptoms, special conditions or special qualifications. The pharmacist or physician can then choose whether to download the interaction warnings to the patient component on operation 214. Alternatively, the system may be designed to automatically download the interaction information to the patient component 104.

The interaction testing scheme described above is a simple, two pass query system which is a binary interaction model where drug A reacts with drug B with a numeric severity code C. It cannot recognize or represent interactions between three or more drugs. The severity code of 1 to 5 representing 1 as a mild interaction and 5 as a potentially fatal interaction may be expanded in a number of ways. For example, symptomatic information may be included in the coding.

Future embodiments of the present invention are envisioned which include a rule based system created to model actual real world interactions on a more complex level. A table in such a relational database would contain a list of all known interactions, their severity, and symptoms. A related table would contain a list of conditions which must be met before the interaction could occur. These conditions might include such things as the substance, the dosages or drug concentrations, frequency of dose administration limitations, and conditional qualifiers. The qualifier "Mandatory", for example, would indicate that the condition must be met in order for an interaction to take place at all. This might be reserved for prescription drugs. A qualifier of "Potential" would indicate that the substance is not controlled or regulated, but could still cause an interaction if ingested. This could, for example, apply to over the counter medications, common or uncommon chemicals and herbal supplements.

In this case, to inquire whether or not an interaction could occur, a query would be run to determine which rules could potentially be filled by the patient's prescription list or OTC medications. The resultant set is then processed sequentially to determine which, if any, rules have been met, and whether or not all of the mandatory rules have been met for any given interaction. Interactions for which all of the mandatory rules are met and for which any conditional rules exist are reported as interactions.

Figure 32:
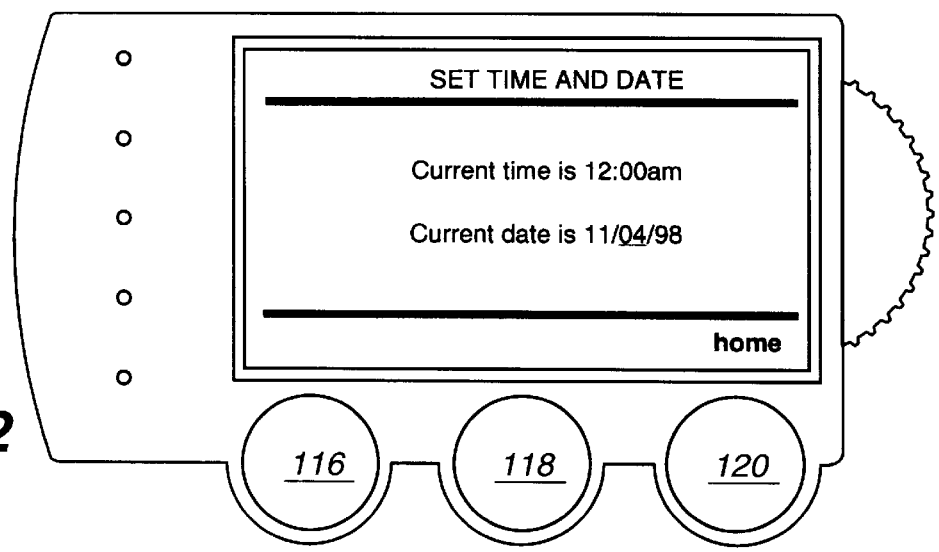
Figure 33:
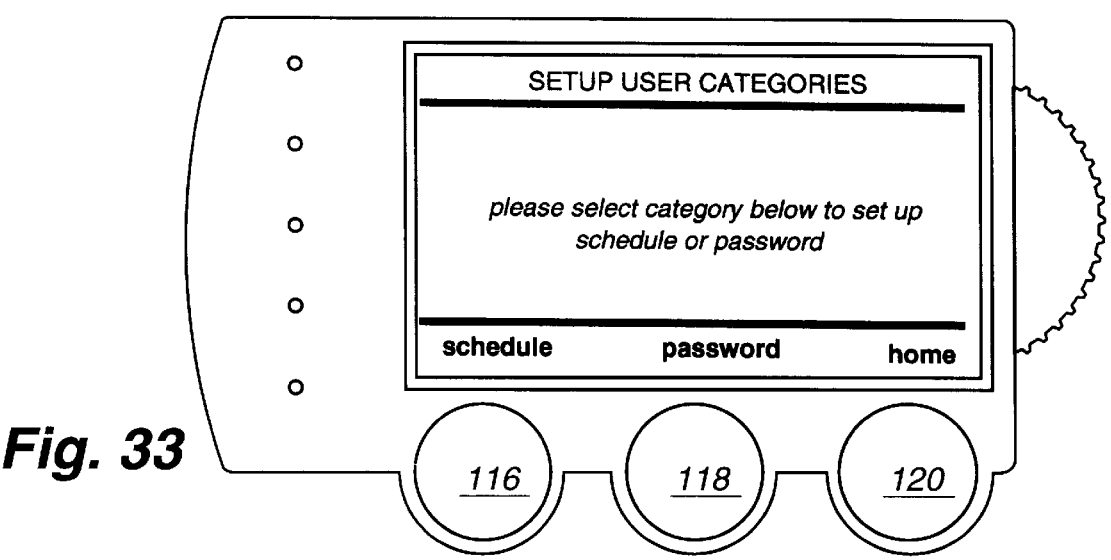
Figure 34:
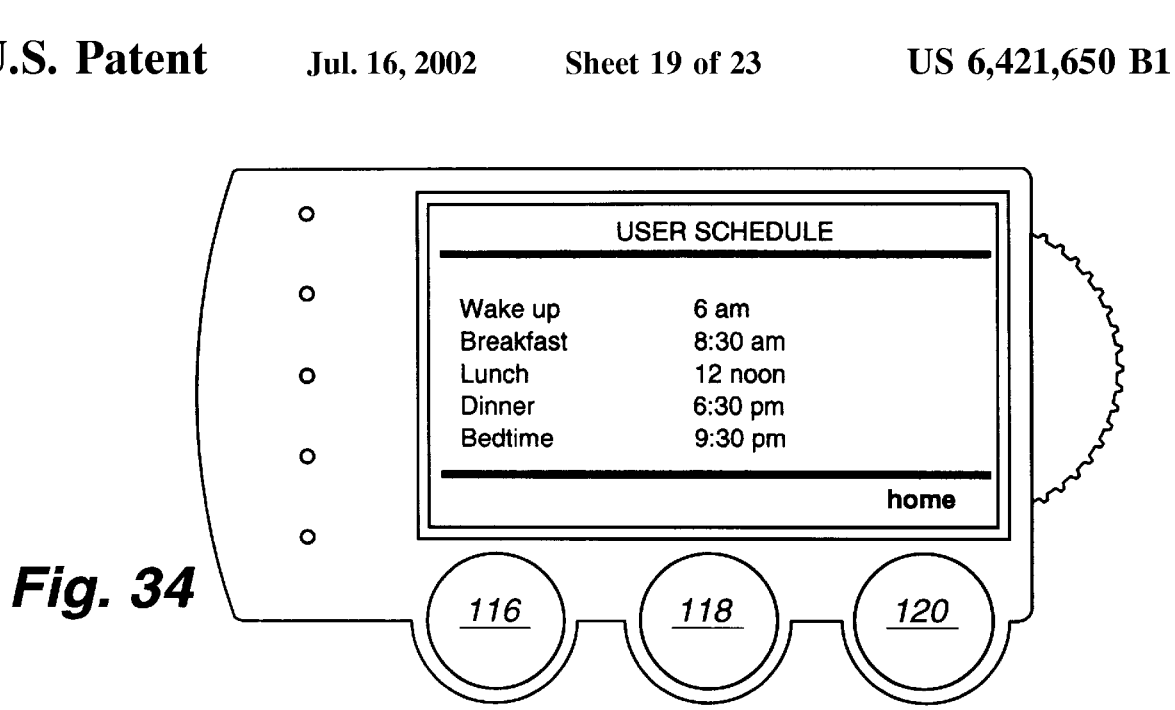
Figure 35:
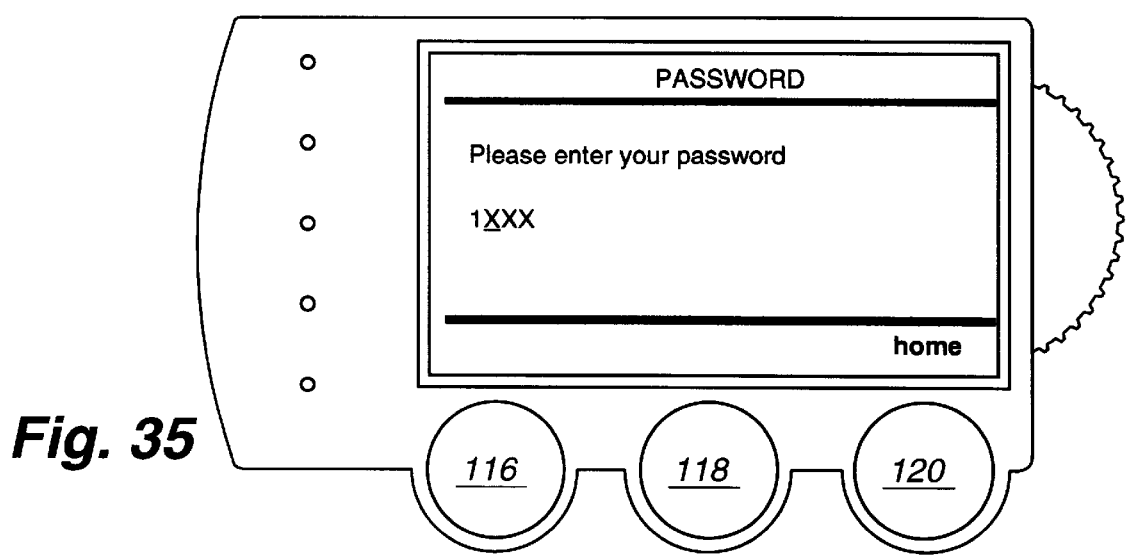

A physician component 102 would then report the interaction, if identified, as shown in FIG. 32 above, and still permit the drug to be prescribed. If this drug is prescribed, a specific caution note would preferably be generated and downloaded to the patient component 104 describing the interaction.

While there have been described above the principles of the present invention in conjunction with specific embodiments thereof, it is to be clearly understood that the foregoing description is made only by way of example and not as a limitation to the scope of the invention. For example, the housing 112 of the patient component 104 may be further miniaturized and accommodated in a large wristwatch sized housing, with the buttons 116, 118, and 120 and wheel 124 provided by peripheral buttons around the housing and display like on a digital watch face. As in the second embodiment above described, the data contained in the database of the patient component 104 would typically be transferred to and from the pharmacist component 106 and the physician component 102 via an infrared communication link as is conventionally known and used in some digital watches.

Another variation of the present invention may include the capability for the patient to enter over the counter (OTC) medication data into the patient component 104. This alternative would preferably also include internal storage for a database of potential interactions downloaded from the physician component 102 or pharmacist component 106 covering the particular medications inputted into the patient component 104. The patient can then enter the name and dosage amount as well as dosage frequency for any OTC medications that he or she may choose to consume. In this instance, the patient component 104 would then query the scheduler and internal database of currently prescribed medications to determine whether there are any special instructions, cautions, or adverse interaction warnings that should be displayed to the patient involving interaction of the OTC medication with prescribed medications.

Particularly, it is recognized that the teachings of the foregoing disclosure will suggest other modifications to those persons skilled in the relevant art. Such modifications may involve other features which are already known per se and which may be used instead of or in addition to features already described herein. It is also to be recognized that the interactions between prescription medications, OTC medications, herbal supplements, and other chemicals need not be detrimental to be identified. The databases utilized may include helpful or complementary interactions between such substances and the program utilized to identify and flag to the patient, pharmacist, or physician those combinations of medications which are or may be enhanced by being administered in combination. The interaction identification program resident in the pharmacist component 106, the physician component 102 and/or the patient component 104 may also be expanded to identify those combinations of three or more medications or chemicals which could precipitate an interaction that the patient should consider. Although claims have been formulated in this application to particular combinations of features, it should be understood that the scope of the disclosure herein also includes any novel feature or any novel combination of features disclosed either explicitly or implicitly or any generalization or modification thereof which would be apparent to persons skilled in the relevant art, whether or not such relates to the same invention as presently claimed in any claim and whether or not it mitigates any or all of the same technical problems as confronted by the present invention. The applicant hereby reserves the right to formulate new claims to such features and/or combinations of such features during the prosecution of the present application or of any further application derived therefrom.

What is claimed is:

1. A medication management system to assist patient control, monitoring and management of administration of prescribed medications comprising:
    a patient component having a retrievable patient database of patient medical history, prior prescribed medications and current prescribed medications, said patient component including a data transfer interface;
    a physician component having a retrievable physician's database of medication information and an input/output device enabling a prescribing physician to enter prescription information into the physician component, said physician's database being capable of receiving and storing patient data transferred from said patient component through said data transfer interface; and
    a pharmacist component resident on a pharmacist's computer, said pharmacist's computer being adapted to interface with said patient component to transfer prescription data to said pharmacist component.

2. The system according to claim 1 wherein said patient component includes a housing containing a microprocessor, a database, a display screen, a programmable alarm clock, and an input device for entering commands to said microprocessor and selecting information to be displayed on said display screen.

3. The system according to claim 1 wherein said patient component is sized to be carried by a patient.

4. The system according to claim 2 wherein said patient component comprises a generally rectangular plastic housing having a liquid crystal display screen and a plurality of control buttons accessible on an exterior of said housing.

5. The system according to claim 4 wherein said housing has a set of three control buttons positioned along one edge of said housing.

6. The system according to claim 1 wherein said physician component is a personal digital assistant.

7. The system according to claim 1 wherein said pharmacist component is a program resident in a pharmacist's personal computer.

8. The system according to claim 1 wherein each of said physician and pharmacist components communicates with said patient component via an infrared interface.

9. The system according to claim 1 wherein said patient component includes a programmed alarm clock prompting a patient to select whether to take a medication dose, delay taking said medication dose, or skip taking said medication dose.

10. The system according to claim 9 wherein said patient component program displays a warning to a patient if said patient selects a delay or skip of a particular medication dose that is impermissible in accordance with predetermined conditions.

11. The system according to claim 9 wherein the patient component, after announcing an alarm condition, automatically logs time and date and whether a patient selects take, delay or skip for a particular medication dose.

12. The system according to claim 9 wherein said patient component reschedules a subsequent alarm time for administration of a permissibly delayed medication dose.

13. The system according to claim 1 wherein the patient component automatically logs the time and date of a patient's response to each alarm for an administration of a medication dose and decrements a memory location containing a number representative of remaining doses of said medication.

14. The system according to claim 13 wherein said patient component automatically terminates scheduling a medication dose when the total dosage of the medication as been administered.

15. A medication management system to assist a patient control, monitor and manage administration of prescribed medications comprising:
    a patient component containing a retrievable patient database of patient medical history, prior prescribed medications and current prescribed medications, said patient component including a display, a clock, a microprocessor, and a data transfer interface and permitting a patient to select and track whether to take a medication dose, delay taking said medication dose, or skip taking said medication dose in response to an alarm generated by said clock; and
    a physician component having a retrievable physician's database of medication information and an input/output device enabling a prescribing physician to enter prescription information into the physician component, said physician's database being capable of receiving and storing patient data transferred from said patient component through said data transfer interface.

16. The system according to claim 15 wherein said patient component includes a housing containing an LCD display screen and an input device for entering commands to said microprocessor and selecting information to be displayed on said display screen.

17. The system according to claim 16 wherein said patient component is sized to be carried by a patient.

18. The system according to claim 17 wherein said patient component comprises a generally rectangular plastic housing having a liquid crystal display screen and a plurality of control buttons accessible on an exterior of said housing.

19. The system according to claim 18 wherein said housing has a set of three control buttons positioned along one edge of said housing.

20. The system according to claim 15 wherein said physician component is a personal digital assistant having a Microsoft Windows type of operating system therein.

21. A medication management system to assist a patient control, monitor and manage administration of prescribed medications comprising:
- a patient component containing a retrievable patient database of patient medical history, prior prescribed medications and current prescribed medications, said patient component including a display, a clock, a microprocessor, and a data transfer interface;
- a physician component having a retrievable physician's database of medication information and an input/output device enabling a prescribing physician to enter prescription information into the physician component, said physician's database being capable of receiving and storing patient data transferred from said patient component through said data transfer interface; and
- a pharmacist component resident on a pharmacist's computer, said pharmacist's computer being adapted to interface with said patient component to receive prescription data from said physician component via said patient component.

22. The system according to claim 21 wherein said pharmacist component is a program resident in a pharmacist's personal computer.

23. The system according to claim 21 wherein each of said physician and pharmacist components communicates with said patient component via an infrared interface.

24. The system according to claim 21 wherein said physician component and/or said pharmacist component includes a subroutine to identify potential interactions between a new medication being prescribed to a patient and a medication currently prescribed to said patient.

25. The system according to claim 24 wherein a warning of said potential interaction may be selectively downloaded from either said pharmacist component or said physician component to said patient component for display on said patient component display screen when an alarm condition occurs for a medication associated with said potential interaction.

26. A medication management system to assist a patient control, monitor and manage administration of prescribed medications comprising:
- a patient component containing a retrievable patient database of patient medical history, prior prescribed medications and current prescribed medications, said patient component including a display, a clock, a microprocessor, and a data transfer interface; and
- a physician component having a retrievable physician's database of medication information and an input/output device enabling a prescribing physician to enter prescription information into the physician component, said physician's database being capable of receiving and storing patient data transferred from said patient component through said data transfer interface wherein said patient component includes a programmed alarm clock permitting a patient to select whether to take a medication dose, delay taking said medication dose, or skip taking said medication dose.

27. The system according to claim 26 wherein said patient component includes an internal a program which displays a warning to a patient if said patient selects a delay or skip of a particular medication dose that is impermissible in accordance with predetermined conditions.

28. The system according to claim 26 wherein the patient component, after announcing an alarm condition, automatically logs time and date and whether a patient selects take, delay or skip for a particular medication dose.

29. The system according to claim 26 wherein said patient component reschedules a subsequent alarm time for administration of a permissibly delayed medication dose.

30. The system according to claim 26 wherein the patient component automatically logs the time and date of a patient's response to each alarm by said programmed alarm clock for an administration of a medication dose and decrements a memory location containing a number representative of remaining doses of said medication.

31. The system according to claim 30 wherein said patient component automatically terminates scheduling a medication dose when the total dosage of the medication has been administered.

32. An apparatus for tracking and monitoring administration of a plurality of medications comprising:
- a hand held portable patient component having generally rectangular hollow plastic housing containing a liquid crystal display, an alarm clock, a microprocessor, a power supply, an input device and a data transfer device, said housing being adapted to receive therein a removable memory device having a database resident thereon, said data transfer device being connectable to said removable memory device in order to display data stored on said removable memory device and transfer scheduling information on said plurality of medications to said microprocessor, said patient component permitting a patient to select whether to take a medication dose, delay taking said medication dose, or skip taking said medication dose and tracking whether the patient takes, delays or skips taking the medication dose.

33. The apparatus according to claim 32 further comprising a physician component adapted to receive and program said removable memory device with prescription information and medical information.

34. The apparatus according to claim 33 wherein said removable memory device is adapted to be read in a pharmacist's computer in order to transfer prescription information from said physician component via said removable memory device.

35. The apparatus according to claim 34 wherein said physician component and said pharmacist's computer are each programmed to process prescription information against at least one medication database to identify potential adverse medication interactions and selectively download an interaction warning to said removable memory device for subsequent display on said patient component.

36. The apparatus according to claim 32 wherein said input device includes a plurality of buttons on said housing for selecting between options presented on said display.

37. The apparatus according to claim 36 further comprising a rocker wheel switch on said housing for scrolling through one or more display screens on said liquid crystal display.

38. The apparatus according to claim 32 wherein said patient component further comprises a database containing potential adverse medication interactions between a prescribed medication and an over-the-counter medication, said over-the-counter medication's identity being entered by a user, and said patient component being programmed to compare prescription medication interaction information to over-the-counter medication interaction information.

39. The apparatus according to claim 32 wherein said patient component may be programmed to allow a user to modify the scheduled administration of the scheduled dosage of medication.

40. The apparatus according to claim 39 wherein the patient component may be programmed to reschedule the administration of said dosage of medication when the user modifies the scheduled administration of said dosage of medication.

41. The apparatus according to claim 39 wherein the patient component may be programmed to prohibit the user from modifying the scheduled administration of said dosage of medication when a possible adverse interaction may result from the modification.

42. The apparatus according to claim 40 wherein the patient component may be programmed to reschedule the administration of said dosage of medication according to the possible adverse interaction with a previous dosage of medication or a subsequent dosage of medication.

43. The apparatus according to claim 40 wherein the patient component may be programmed to reschedule a subsequent dosage of medication when the user modifies the scheduled administration of said dosage of medication.

44. An apparatus for tracking and monitoring administration of a plurality of medications to a patient, said apparatus including a patient component, a physician component and a pharmacist component, said patient component comprising:

a generally rectangular hollow plastic housing containing a microprocessor connected to a liquid crystal display, an alarm clock, a power supply, an input device, a patient's database stored in a memory, and a data transfer device, said data transfer device being connectable to said physician component and/or said pharmacist component to transfer scheduling information on said plurality of medications to said microprocessor, said patient component permitting a patient to select whether to take a medication dose, delay taking said medication dose, or skip taking said medication dose in response to an alarm produced by said alarm clock.

45. The apparatus according to claim 44 wherein said physician component contains a physician's database of medications, a program usable by a physician to prescribe one or more medications to a patient, and a program for comparing said one or more medications with said physician's database of medications to identify and display interactions between said one or more medications being prescribed and another medication.

46. The apparatus according to claim 44 wherein said physician component contains a database of medications, a program usable by a physician to prescribe one or more medications to a patient and download said prescribed medication to said patient component.

47. The apparatus according to claim 46 wherein one of said patient component, said physician component, or said pharmacist component includes a program for comparing a prescribed medication to a database of medications to identify and display at least one interaction identified between said prescribed medication and another medication.

48. The apparatus according to claim 47 wherein said pharmacist component has access to said database of medications and said program for comparing a prescribed medication to said database.

49. An apparatus for tracking and monitoring administration of a plurality of medications to a patient, said apparatus including a patient component, a physician component and a pharmacist component, said patient component having generally rectangular hollow plastic housing containing a microprocessor connected to a liquid crystal display, an alarm clock, a power supply, an input device, a patient's database stored in a memory, and a data transfer device, said data transfer device being connectable to said physician component and/or said pharmacist component to transfer scheduling information on said plurality of medications to said microprocessor, said physician component containing a database of medications, a program usable by a physician to prescribe one or more medications to a patient and download said prescribed medication to said patient component, wherein one of said patient component, said physician component, or said pharmacist component includes a program for comparing a prescribed medication to a database of medications to identify and display at least one interaction identified between said prescribed medication and another medication, said patient component including another program for comparing a prescribed medication to a database of medications stored in said patient component to identify an interaction between said prescribed medication and another medication.

50. The apparatus according to claim 45 wherein said physician component is adapted to communicate said prescribed medication and said interaction to said patient component via said data transfer device.

51. The apparatus according to claim 50 wherein each of said physician component and said patient component includes an infrared data transfer device for communicating data therebetween.

52. The apparatus according to claim 44 wherein said pharmacist component is a software program resident on a pharmacist's computer, said program including a program for comparing said one or more medications with a database of medications to identify and display interactions between said one or more medications being prescribed and another medication.

53. The apparatus according to claim 52 wherein said patient component communicates a patient's current prescribed medication data to said pharmacist component and to said physician component through an infrared data transfer device.

54. The apparatus according to claim 53 wherein said patient component database includes current medications and current medication dose schedules.

55. The apparatus according to claim 54 wherein said patient component stores and tracks in said database a patient's responses to an alarm for administration of a medication.

56. The apparatus according to claim 55 wherein said patient component can optimize scheduling of administration of medication to a patient based on said patient's daily schedule of activity.

* * * * *